(12) United States Patent
Kanayinkal et al.

(10) Patent No.: US 9,096,839 B2
(45) Date of Patent: Aug. 4, 2015

(54) COMPOSITIONS AND METHODS OF PREPARATION THEREOF

(75) Inventors: Tessy Kanayinkal, Brooklyn Park, MN (US); Laura A. Yonce, Edina, MN (US); Debra Mullins-Hirte, Oakdale, MN (US); Trevor C. Huang, Maple Grove, MN (US); Rohit Cariappa, Bangalore (IN); Kenneth E. Merte, Southlake, TX (US); James R. Keogh, Maplewood, MN (US); Kevin D. McIntosh, Brooklyn Park, MN (US); Brian J. Steffens, Maple Grove, MN (US); Asha S. Nayak, Santa Rosa, CA (US); Erick L. Johnson, Mpls, MN (US)

(73) Assignee: Arteriocyte Medical Systems, Inc., Cleveland, OH (US)

( * ) Notice: Subject to any disclaimer, the term of this patent is extended or adjusted under 35 U.S.C. 154(b) by 1414 days.

(21) Appl. No.: 11/796,045

(22) Filed: Apr. 26, 2007

(65) Prior Publication Data

US 2008/0044852 A1 Feb. 21, 2008

Related U.S. Application Data

(60) Provisional application No. 60/794,971, filed on Apr. 26, 2006.

(51) Int. Cl.
*C12N 9/74* (2006.01)
*C12N 5/078* (2010.01)
*A61K 35/16* (2015.01)
*A61K 35/19* (2015.01)
*A61K 35/14* (2015.01)
*C07K 14/745* (2006.01)

(52) U.S. Cl.
CPC .............. *C12N 9/6429* (2013.01); *A61K 35/14* (2013.01); *A61K 35/16* (2013.01); *A61K 35/19* (2013.01); *C07K 14/745* (2013.01); *C12N 5/0644* (2013.01); *C12Y 304/21005* (2013.01)

(58) Field of Classification Search
None
See application file for complete search history.

(56) References Cited

U.S. PATENT DOCUMENTS

| | | | |
|---|---|---|---|
| 4,627,879 A | 12/1986 | Rose et al. | |
| 4,874,368 A | 10/1989 | Miller et al. | |
| 5,104,375 A | 4/1992 | Wolf et al. | |
| 5,165,938 A | 11/1992 | Knighton | |
| 5,185,001 A | 2/1993 | Galanakis | |
| 5,354,682 A | 10/1994 | Kingdon et al. | |
| 5,391,380 A | 2/1995 | Barrow et al. | |
| 5,474,540 A | 12/1995 | Miller et al. | |
| 5,510,102 A | 4/1996 | Cochrum | |
| 5,585,007 A | 12/1996 | Antanavich et al. | |
| 5,589,462 A | 12/1996 | Patat et al. | |
| 5,607,694 A | 3/1997 | Marx | |
| 5,643,192 A | 7/1997 | Hirsh et al. | |
| 5,733,545 A | 3/1998 | Hood, III | |
| 5,738,784 A | 4/1998 | Holm et al. | |
| 5,739,288 A | 4/1998 | Edwardson et al. | |
| 5,750,657 A | 5/1998 | Edwardson et al. | |
| 5,773,418 A | 6/1998 | Edwardson et al. | |
| 5,788,662 A | 8/1998 | Antanavich et al. | |
| 5,795,571 A | 8/1998 | Cederholm-Williams et al. | |
| 5,795,780 A | 8/1998 | Cederholm-Williams et al. | |
| 5,814,022 A | 9/1998 | Antanavich et al. | |
| 5,962,420 A | 10/1999 | Edwardson et al. | |
| 6,048,966 A | 4/2000 | Edwardson et al. | |
| 6,054,122 A | 4/2000 | MacPhee et al. | |
| 6,063,297 A | 5/2000 | Antanavich et al. | |
| 6,071,514 A | 6/2000 | Grinnell et al. | |
| 6,077,507 A | 6/2000 | Edwardson et al. | |
| 6,110,721 A | 8/2000 | Gibbs et al. | |
| 6,113,571 A | 9/2000 | Zinger et al. | |
| 6,117,425 A | 9/2000 | MacPhee et al. | |
| 6,132,396 A | 10/2000 | Antanavich et al. | |
| 6,197,194 B1 | 3/2001 | Whitmore | |
| 6,197,325 B1 | 3/2001 | MacPhee et al. | |
| 6,200,587 B1 | 3/2001 | Soe et al. | |
| 6,214,338 B1 | 4/2001 | Antanavich et al. | |
| 6,444,228 B1 | 9/2002 | Baugh et al. | |
| 6,472,162 B1 | 10/2002 | Coelho et al. | |
| 6,596,180 B2 | 7/2003 | Baugh et al. | |
| 6,719,901 B2 | 4/2004 | Baugh et al. | |
| 6,830,762 B2 | 12/2004 | Baugh et al. | |
| 6,899,813 B2 | 5/2005 | Dolecek et al. | |
| 6,942,639 B2 | 9/2005 | Baugh et al. | |
| 6,942,880 B1 | 9/2005 | Dolecek et al. | |
| 7,009,034 B2 * | 3/2006 | Pathak et al. | ................ 530/200 |
| 2002/0004038 A1 | 1/2002 | Baugh et al. | |

(Continued)

FOREIGN PATENT DOCUMENTS

| | | |
|---|---|---|
| EP | 0443724 A1 | 8/1991 |
| EP | 0443724 B1 | 8/1991 |

(Continued)

OTHER PUBLICATIONS

Kumar et al., "Stability of Human Thrombin Produced from 11 ml of Plasma Using the Thrombin Processing Device", Journal of Extra-Corporeal Technolgy 25 (4) : 390-395 (2005).*
Ren et al., "Effects of complex of rhBMP2 and fibrin sealant on dental pulp", Zhonghua koudian Yixue Sashi 35 (1) : 18-20 (2000), English abstract only.*
Thorn et al., "Autologous fibrin glue with growth factors in reconstructive maxillofacial surgery", Int. J. Oral. Maxillofac. Surg. 33 : 95-100 (2004).*
"Simultaneous Occurrence of Human Antibodies Directed against Fibrinogen, Thrombin, and Factor V Following Exposure to Bovine Thrombin: Effects on Blood Coagulation, Protein C Activation and Platelet Function," Vibhuti D. Chouhan, Raul A. De La Cadena, Chandrasekaran Nagaswami, John W. Weisel, Mehdi Kajani, and A. Koneti Rao, Thrombosis and Haemostasis, 77(2): 343-9 (1997).

(Continued)

*Primary Examiner* — Allison Fox
*Assistant Examiner* — Susan E Fernandez
(74) *Attorney, Agent, or Firm* — Mintz Levin Cohn Ferris Glovsky and Popeo, P.C.

(57) ABSTRACT

The present invention provides biological compositions and methods for making the same.

16 Claims, 7 Drawing Sheets

(56) References Cited

U.S. PATENT DOCUMENTS

| | | |
|---|---|---|
| 2004/0132003 A1 | 7/2004 | Baugh et al. |
| 2004/0213777 A1 | 10/2004 | Baugh et al. |
| 2005/0129674 A1 | 6/2005 | Baugh et al. |
| 2005/0152886 A1 | 7/2005 | Baugh et al. |
| 2005/0170006 A1 | 8/2005 | Baugh et al. |
| 2005/0209081 A1 | 9/2005 | Baugh et al. |
| 2005/0236325 A1 | 10/2005 | Dolecek et al. |
| 2005/0252867 A1 | 11/2005 | Baugh et al. |
| 2006/0029679 A1 | 2/2006 | Dolecek |

FOREIGN PATENT DOCUMENTS

| | | |
|---|---|---|
| EP | 0592242 A1 | 4/1994 |
| EP | 0858775 A1 | 2/1998 |
| WO | WO 91/09573 | 7/1991 |
| WO | WO 94/07548 | 4/1994 |
| WO | WO 96/17871 | 6/1996 |
| WO | WO 96/27397 | 9/1996 |
| WO | WO 96/31245 | 10/1996 |
| WO | WO 97/29792 | 8/1997 |
| WO | WO 97/40864 | 11/1997 |
| WO | WO 99/18931 | 4/1999 |
| WO | WO 99/66797 | 12/1999 |
| WO | WO 00/07659 | 2/2000 |
| WO | WO 00/62828 | 10/2000 |
| WO | WO 00/74713 | 12/2000 |
| WO | WO 02/10989 | 2/2002 |
| WO | WO 02/080991 | 10/2002 |

OTHER PUBLICATIONS

"Severe Bleeding due to Factor V. Inhibitor after Repeated Operations Using Fibrin Sealant containing Bovie Thrombin," W. Muntean, W. Zenz, G. Edlinger, and A. Beitzke, Thrombosis and Haemostatsis, 77:1223 (1997).

Postoperative Bleeding Induced by Topical Bovine Thrombin: Report of Two Cases, Robert J. Christie, MC, Leonthena Carrington, BS, and Barbara Alving, MD, Surgery, 121(6): 708-710 (Jun. 1977).

"Fibrin Sealant: Summary of a Conference on Characteristics and Clinical Uses," B.M. Alving, M.J. Weinstein, J.S. Finlayson, J.E. Menitove, and J.C. Fratantoni, Transfusion, 35: 783-790 (1995).

"Inhibitor to Factor V after Exposure to Fibrin Sealant During Cardiac Surgery in a Two Year Old Child," W. Muntean, W. Zenz, K. Finging, G. Zobel and A. Beitzke, Acta Pediatr, 83:84-7 (1994).

"Immunization by Bovine Thrombin Used With Fibrin Glue During Cardiovascular Operations," Micheline Berruyer, BS, Jean Amiral, Ph.D., Patrick French, MD, Jean Belleville, MD, Olivier Bastien, MD Jean Clerc, MD, Alain Kassir, MD, Susanne Estavnove, MD and Marc Dechavanne, MD, The Journey of Thoracic and Cardiovascular Surgery, 105(5): 892-897 (May 1993).

"An Anaphylactic Reaction to Topical Fibrin Glue," Hiromasa Mitsuhata, MD, Yuji Horiguchi, MD, Kazuhiko Saitoh, MD, Hirokazu Fukuda, MD, Yosihiro Hirabayasi, MD, Hideaki Togashi, MD, and Reiju Shimizu, MD, Anesthesiology, 81(4): 1074-1077 (Oct. 1994).

"Anaphylactic Reaction to Topical Bovine Thrombin," David M. Rothenberg, MD and James N. Moy, MD, Anesthesiology, 78(4) 779-782 (Apr. 1993).

"Clinical Significance of Antibodies to Bovine and Human Thrombin and Factor V After Surgical Use of Bovine Thrombin," Samuel I. Rapaport, MD, Ariella Zivelin, M.Sc., Robert A. Minow, MD, Christine S. Hunter, MD, and Kathleen Donnelly, MS, A.J.C.P.,97(1): 84-91 (Jan. 1992).

"Development of Antibodies to Thrombin and Factor V With Recurrent Bleeding in a Patient Exposed to Topical Bovine Thrombin," James L. Zehnder, and Lawrence L.K. Leung, Blood, 76(10): 1011-1016 (Nov. 15, 1990).

"An Anaphylactic Reaction to Fibrin Glue," Leslie Newberg Milde, MD, Anesth Analg, 69:684-6 (1989).

"Iatrogenic Immunization with Bovine Thrombin: A Mechanism for Prolonged Thrombin Times after surgery." Michael J. Flaherty, MD, Ruth Henderson, MD, and Mark H. Wener, MD, Annuals of Internal Medicine, 111(8): 631-634 (Oct. 15, 1989), English abstract only.

"Clinical Application of the Fibrin Adhesive," Suzuki, M., et al., Otolaryngology, 56(11) 949-953 (1984), Tokyo.

"Preparation and Properties of Serum and Plasma Proteins, IV. A System for the Separation into Fractions of the Protein and Lipoprotein Components of Biological Tissues and Fluids," Cohn et al. J. Am. Chem. Soc. 68:459-457 (1946).

"The Separation of the Antibodies, Isoagglutinins, Prothrombin, Plasminogen and B-Lipoprotein into Subfractions of Human Plasma," Oncley et al., J. Am. Chem. Soc., 71:541-550 (1949).

Diquelou et al., Thrombosis and Haemostasis, 74: 778-783 (1995).

Nemerson, Thrombosis and Haemostasis, 74: 180-184 (1995).

Marieb, Human Anatomy & Physiology, $2^{nd}$ Ed., Benjamin/ Cummings, California, 1992, pp. 576-596.

Hirsh & Brain, Hemostasis & Thrombosis: A Conceptual Approach, $2^{nd}$ Ed., Churchill Livingston (New York), 1983, pp. 5-9, 13, 15, 101-103.

Mann, Thrombosis and Haemostasis, 82: 165-174 (1999).

Buchta et al., Biomaterials, 26 6233-6241 (2005).

van Oss, Journal of Protein Chemistry, 8(5)661-668 (1989).

Kaetsu et al., Thrombosis Research 90:101-109.

International Search Report and Written Opinion from International Application No. PCT/US2007/067494 dated Aug. 3, 2011.

"Can Autologous Thrombin With a Rest Fraction of Ethanol Be Used Safely for Activation of Concentrated Autologous Platelets Applied on Nerves?" Filip De Somer, Veerle De Brauwer, Maxence Vanderkerckhove, Richard Ducatelle, Dirk Uyttendaele and Guido Van Nooten, European Spine Journal, vol. 15., pp. 501-505 (2006).

"Stability of Human Thrombin Produced From 11 ml of Plasma Using the Thrombin Processing Device," Vijay Kumar, Ph.D., Trista Madsen BS, Haihong Zhu BS, Elisabeth Semple, Ph.D., The Journal of the American Society of Extra-Corporeal Technology, vol. 37, pp. 390-395 (2005).

"Use of a Platelet-Fibrinogen-Thrombin Mixture As a Corneal Adhesive: Experiments With Sutureless Lamellar Keratoplasty in the Rabbit," A. Ralph Rosenthal, Christina Harbury, Peter R. Egbert and Edward Rubenstein, Investigative Ophthalmology, vol. 14, pp. 872-875 (Nov. 1975).

"Whole Blood Thrombin: Development of a Process for Intra-operative Production of Human thrombin," Vijay Kumar, Ph.D. and John R. Chapman, Ph.D., vol. 39, pp. 18-23 (Mar. 2007).

Database Medline [Online] US National Library of Medicine (NLM) Bethesda, MD, US; Ukrainskii Biokhimicheskii Zhurnal, vol. 75, No. 5, pp. 17-27, Sep. 2003.

* cited by examiner

US 9,096,839 B2

COMPOSITIONS AND METHODS OF PREPARATION THEREOF

CROSS-REFERENCE TO RELATED APPLICATION

This application claims the benefit of U.S. provisional patent application Ser. No. 60/794,971, filed Apr. 26, 2006, which is specifically incorporated by reference herein.

BACKGROUND OF THE INVENTION

Blood coagulation is the result of the complex interaction of a number of protein clotting factors that occurs through a cascade (FIG. 1). In general, damage to the vascular endothelium exposes subendothelial structures that attract platelets and induce them to aggregate reversibly. The protein thrombin, formed during activation of the coagulation pathway, generates insoluble crosslinked fibrils of the protein fibrin and causes the platelets to aggregate irreversibly. The resulting platelet-fibrin clot is an effective barrier against loss of blood from the vascular system and also serves as a scaffold for subsequent repair of the lining of the blood vessel.

Different principles for production of fibrin sealants and the like have been established, and commercial devices employing these methods are available and in clinical use. However, there is still a need in the art for biological compositions, e.g., fibrin compositions, and methods for the production thereof.

BRIEF SUMMARY OF THE INVENTION

The present invention is directed to biological compositions and methods for the preparation thereof.

In one embodiment of the invention, a method for preparing a thrombin composition is provided. The method includes contacting whole blood, a component thereof or a fraction thereof, e.g., platelet rich plasma (PRP), platelet poor plasma (PPP), or a combination thereof, with a contact activation agent, e.g., glass wool, an extrinsic coagulation pathway initiation agent, e.g., thromboplastin, or combination thereof, to generate a coagulated mass in less than about thirty minutes, obtaining thrombin from the mass and contacting the thrombin with a stabilizing agent to provide a thrombin composition comprising thrombin having a table-life of more than about six hours. The thrombin may be obtained from whole blood, a component thereof or a fraction thereof that has been collected from composition's recipient. In one embodiment, the whole blood, component thereof or fraction thereof, with a source of calcium ions, e.g., $CaCl_2$ or a salt thereof. The stabilizing agent may include a polyol, PEG, ammonium sulfate, a non-polar solvent, a polar solvent, a methyl isobutyl ketone alcohol, glycol, trichloroacetic acid, acetate salt, and any combination thereof, e.g., ethanol. In one embodiment, the ethanol is in the range of about 8% to about 25% volume/volume, e.g., 10% v/v ethanol. One embodiment of the method includes the proviso that the whole blood, component thereof or fraction thereof, is not contacted with the ethanol prior to generation of the mass. In another embodiment, the mass is generated in less than about 10 minutes, e.g., less than about 5 minutes, less than about 3 minutes, or for example, in about 1 minute to about 3 minutes. The table-life of the thrombin in the thrombin composition may be more than 6 hours, e.g., more than 12 hours, or in another embodiment up to 24 hours. For example, in one embodiment the thrombin composition comprises thrombin having biological activity, e.g., enzymatic activity, for more than six hours. In another embodiment, the thrombin composition, when contacted with fibrinogen, is capable of forming a fibrin sealant composition in about 10 seconds or less. In yet another embodiment, the invention provides the thrombin composition prepared by such a method.

Further provided is a method of preparing a fibrin composition, the method including fractionating anticoagulated whole blood, a fraction thereof or a component thereof, to obtain a composition comprising fibrinogen, and contacting the fibrinogen composition and a thrombin composition to provide a fibrin composition. In one embodiment of the invention, the anticoagulated whole blood, a fraction thereof or a component thereof, is obtained from the fibrin composition's recipient. Another embodiment of the invention further includes obtaining a platelet composition comprising platelet rich plasma, platelet poor plasma, or a combination thereof. In yet another embodiment, plasma proteins present in the platelet composition are concentrated, e.g., by cryoprecipitation, chemical precipitation, filtration, dialysis, chromatography, electrophoresis, dehydration, or a combination thereof, e.g., the plasma proteins are concentrated using ethanol in one embodiment, to provide a plasma protein concentrate, and contacting the concentrate with the fibrinogen composition and the thrombin composition. In one embodiment, the thrombin composition comprises autologous thrombin, recombinant thrombin, bovine thrombin, or a combination thereof. Another embodiment of the method further includes contacting the composition with a recombinantly produced protein. In yet another embodiment, provided is the fibrin composition prepared by such a method.

The present invention also provides a method of preparing a platelet rich fibrin sealant composition, the method including fractionating anticoagulated whole blood, a fraction thereof or a component thereof to obtain a composition comprising platelets, and contacting the platelet composition with a fibrinogen composition, e.g., autologous fibrinogen, recombinant fibrinogen, or a combination thereof, and a thrombin composition, e.g., recombinant thrombin, autologous thrombin, bovine thrombin, or a combination thereof, to provide a platelet rich fibrin sealant composition. One embodiment of the method further involves concentrating, e.g., via filtration methodology, plasma proteins present in the whole blood to provide a protein concentrate, and contacting the platelet composition, the fibrinogen composition and the thrombin composition with the protein concentrate, e.g., which comprises fibrinogen, Factor XIII, Factor VIII, von Willebrand factor (vWF), or a combination thereof. A platelet rich fibrin sealant composition of the invention may also be "fortified" with additional fibrinogen, and may have enhanced mechanical strength as compared to a fibrin sealant composition. Also provided is a platelet rich fibrin sealant composition prepared by such a method.

Further provided herein is a method of preparing a fibrin composition, the method including contacting a first portion of anticoagulated whole blood, a fraction thereof or a component thereof, for example, platelet rich plasma (PRP), platelet poor plasma (PPP), or a combination thereof, with a contact activation agent, e.g., glass wool, and an extrinsic coagulation pathway initiation agent, e.g., thromboplastin, to provide a coagulated mass in less than about 30 minutes, extracting thrombin from the coagulated mass to provide a thrombin composition, fractionating a second portion of the anticoagulated whole blood, a fraction thereof or a component thereof, e.g., platelet rich plasma (PRP), platelet poor plasma (PPP), or a combination thereof, to obtain a fibrinogen composition and a platelet plasma composition, and contacting the thrombin composition, the fibrinogen composition and the platelet composition to generate a fibrin composition. One embodiment of the invention further comprises contacting the fibrinogen composition, platelet composition, or a combination thereof with a recombinant protein composition. Another embodiment further involves contacting the thrombin composition with a stabilizing agent, e.g., a polyol, PEG, ammonium sulfate, a non-polar solvent, a polar solvent, a methyl isobutyl ketone alcohol, glycol, tricloroacetic acid, acetate salt, or any combination thereof, e.g., ethanol, such as about 8% to about 25% volume/volume ethanol, for example, about 10% volume/volume ethanol, to provide a thrombin composition having a table-life of more than about 6 hours. In one embodiment of the method, the thrombin composition has a table-life of more than 12 hours, e.g., up to 24 hours. Yet another embodiment of the method includes the proviso that the anticoagulated whole blood, a fraction thereof or a component thereof is not contacted with ethanol during the generation of the coagulated mass. In an embodiment of the method, the coagulated mass is generated in less than about 10 minutes, for example, less than about 5 minutes, less than about 3 minutes, or in about 1 minute to about 3 minutes. In one embodiment, the anticoagulated whole blood, a fraction thereof or a component thereof is contacted with a source of calcium ions, e.g., $CaCl_2$ or a salt thereof. In another embodiment, the anticoagulated whole blood, a fraction thereof or a component is obtained from the fibrin composition's intended recipient. In one embodiment of the invention, the coagulated mass comprises a fibrin clot. Another embodiment further includes contacting the thrombin composition, the fibrinogen composition and the platelet composition with a pharmaceutical agent, therapeutic agent, medical agent, biological agent, or any combination thereof to provide a fibrin composition. Further provided is the fibrin composition prepared by such a method The details of one or more embodiments of the invention are set forth in the accompanying drawings and the description below. Other features, objects, and advantages of the invention will be apparent from the description and drawings, and from the claims.

DETAILED DESCRIPTION OF THE INVENTION

I. Definitions

Figure 1:
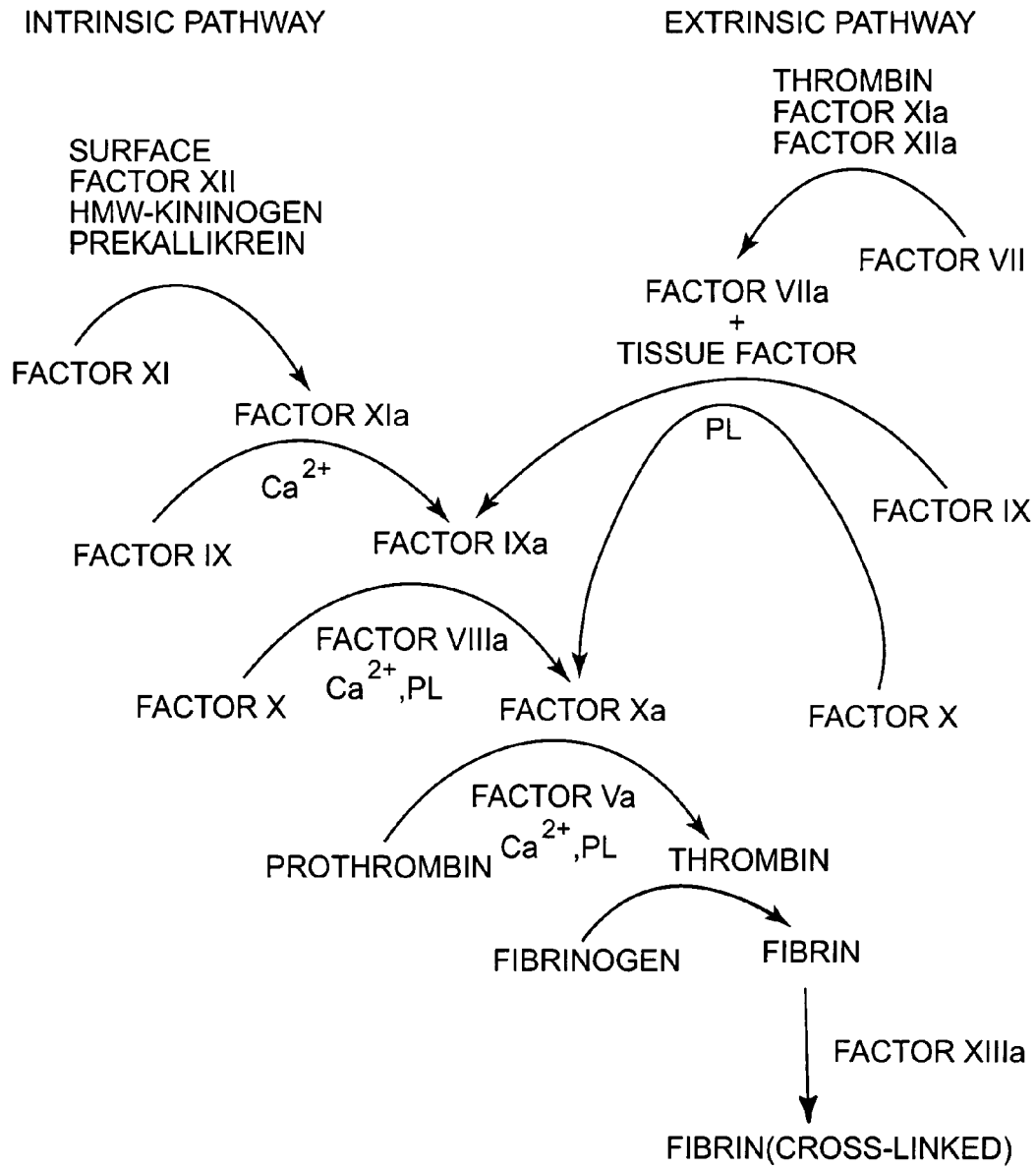
FIG. 1 depicts a coagulation cascade.
Figure 2:
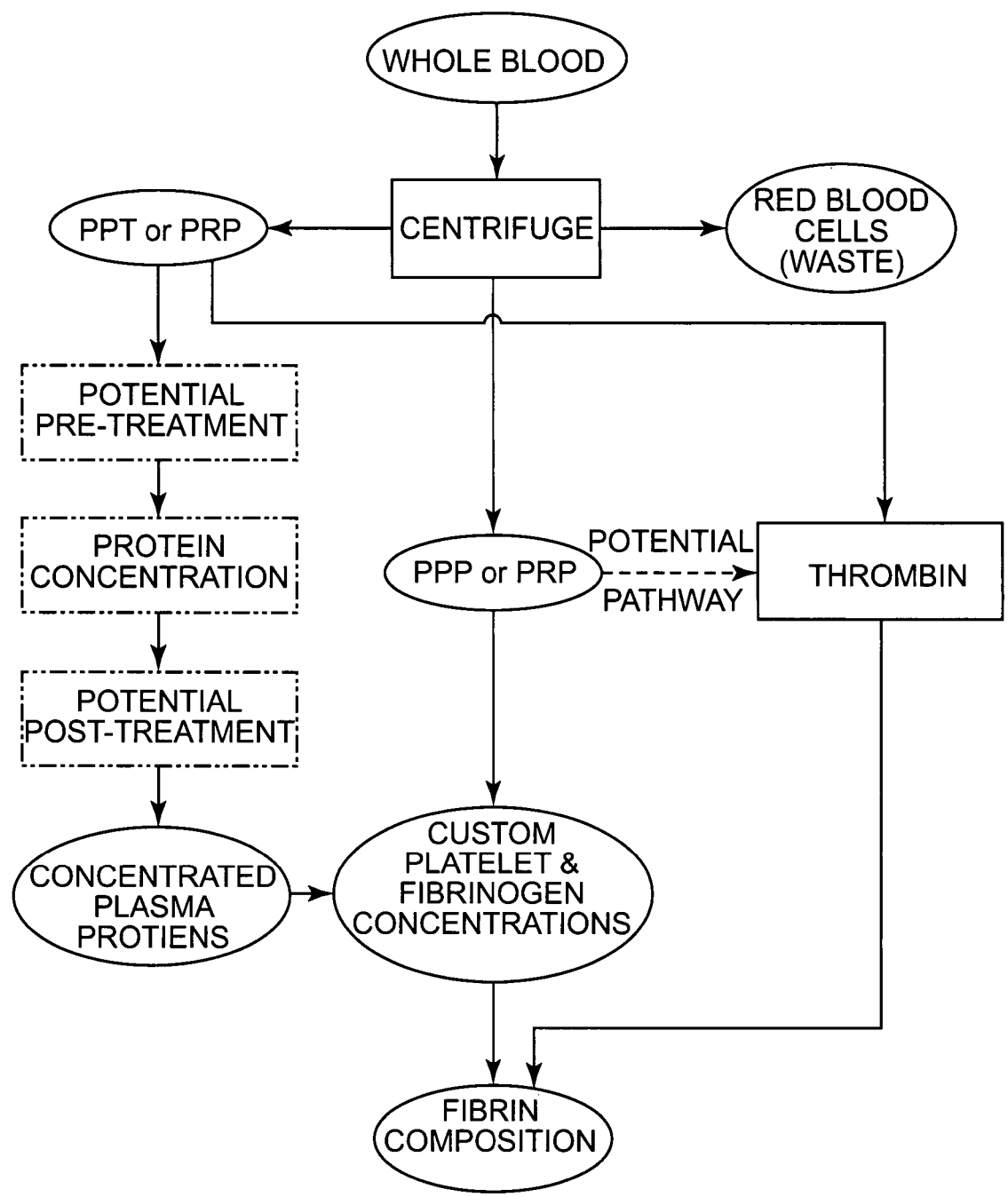
FIG. 2 is a flow diagram of one embodiment in accordance with the present invention.
Figure 3:
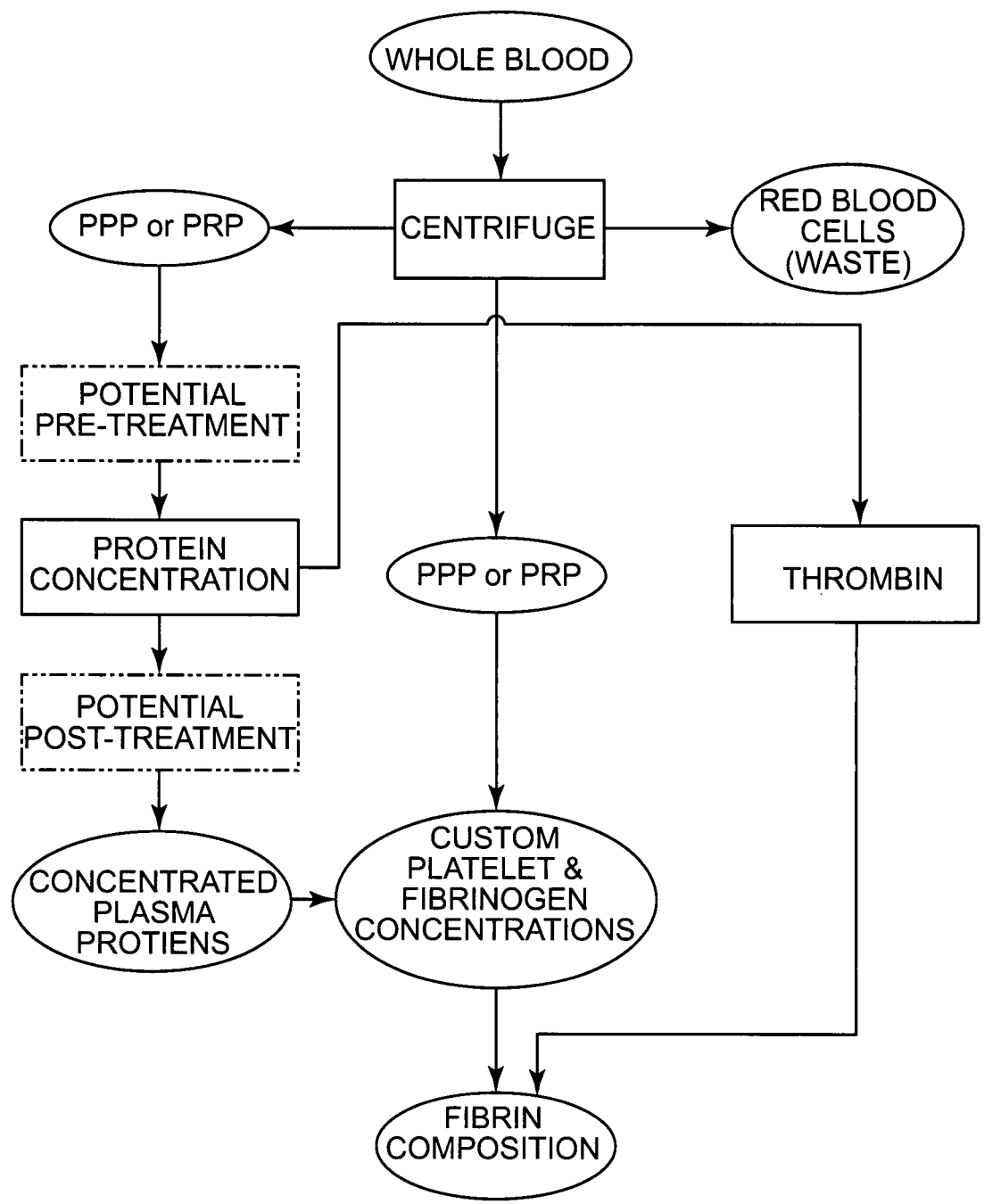
FIG. 3 is a flow diagram of one embodiment in accordance with the present invention.
Figure 4:
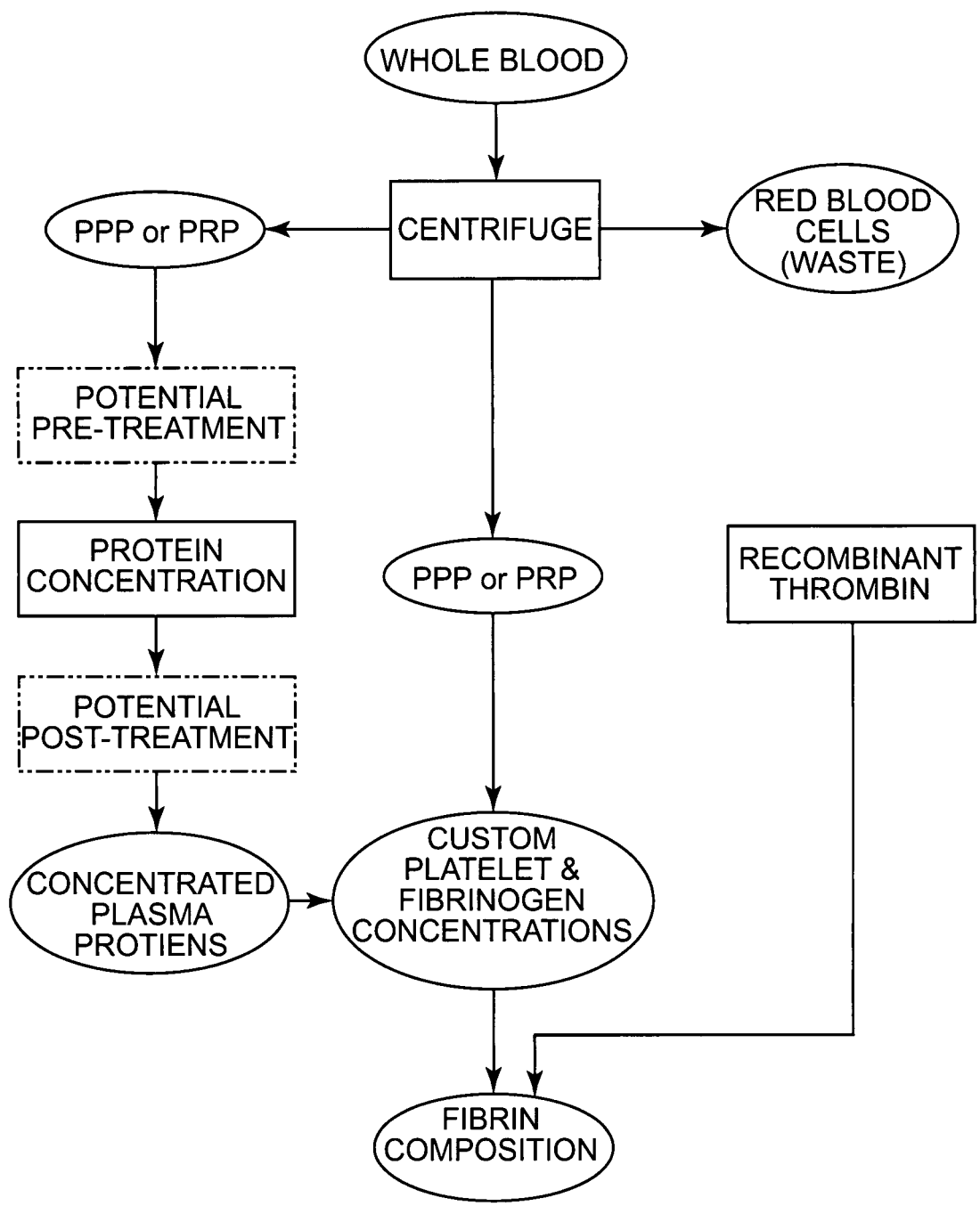
FIG. 4 is a flow diagram of one embodiment in accordance with the present invention.
Figure 5:
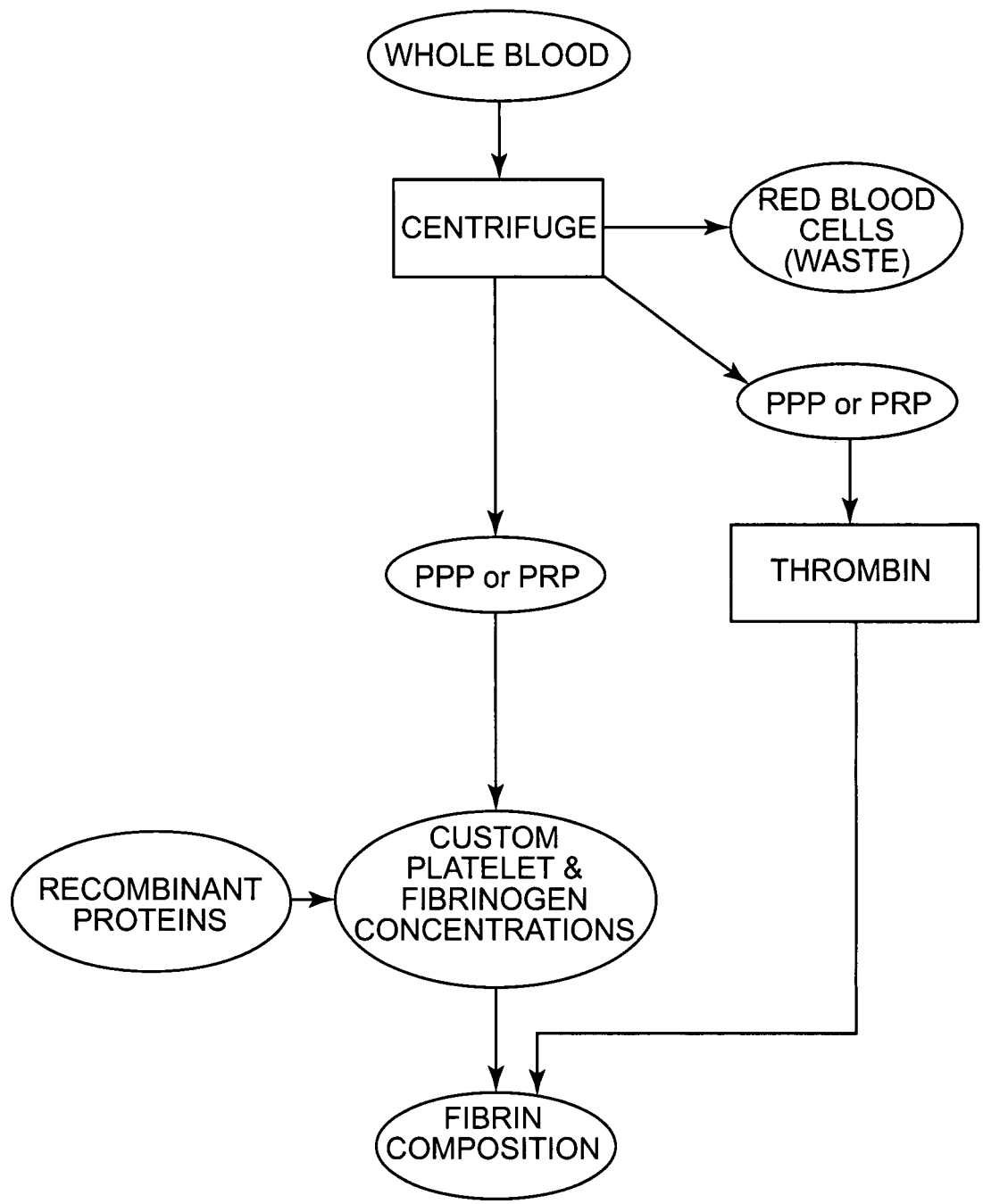
FIG. 5 is a flow diagram of one embodiment in accordance with the present invention.
Figure 6:
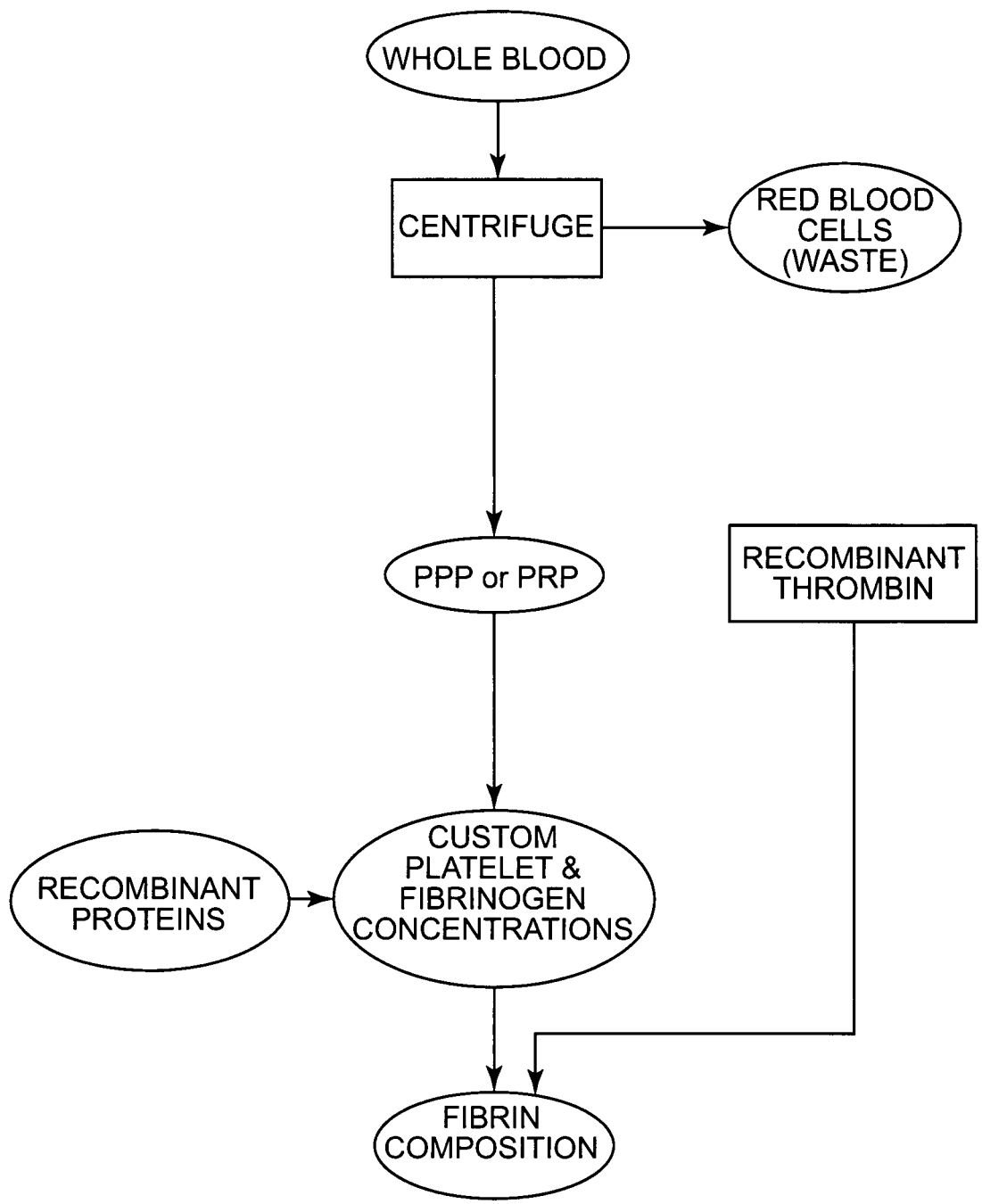
FIG. 6 is a flow diagram of one embodiment in accordance with the present invention.

As used herein, the phrase "fibrin composition" is a composition including at least fibrin, a component thereof, a derivative thereof, a fraction thereof, or a combination thereof. When combined, fibrinogen and thrombin may form a layer of fibrin, i.e., fibrin and fibrin monomers align non-covalently end to end and side by side to form branched fibrin strands and a three-dimensional fibrin network. Thus, fibrin compositions of the present invention may include fibrin, e.g., autologous fibrin, as well as fibrinogen, e.g., autologous fibrinogen, recombinant fibrinogen, and thrombin, e.g., autologous thrombin, recombinant thrombin, bovine thrombin, and the like. For example, one type of fibrin composition of the invention is a "fibrin sealant" that has at least fibrin and thrombin. Fibrin sealants are commercially available, e.g., CRYOSEAL® (Thermogenesis, Rancho Cordova, Calif.), VIVOSTAT® (Vivolution A/S, Birkerod, Denmark), and TISSUCOL/TISSEEL® (Baxter AG, Vienna, Austria).

As used herein, the phrase "autologous fibrin composition" refers to a fibrin composition having components obtained from or derived from the same individual (i.e., the donor) to whom the composition is to be administered (i.e., the recipient). An autologous fibrin composition of the present invention can include autologous fibrin, autologous fibrinogen, autologous thrombin, or a combination thereof, derived from whole blood, a component thereof or a fraction thereof, that was obtained from a patient to whom the composition is to be applied.

Another example of a fibrin composition of the invention is a "platelet rich fibrin sealant" or "PRFS," which refers to a fibrin sealant that includes platelets, e.g., platelet rich plasma (PRP), fibrin and thrombin.

"Platelet rich plasma" or "PRP" refers to plasma having concentrated platelets, i.e., an increased concentration of platelets as compared to native plasma and plasma. PRP may also contain concentrated clotting factors and other proteins, including, but not limited to, fibrinogen, Factor XIII, Factor VIII and von Willebrand factor (vWF).

A "platelet gel" refers to a composition having platelets, e.g., autologous platelets; and thrombin, e.g., autologous thrombin, recombinant thrombin, bovine thrombin. For example, an "autologous platelet gel" or "APG" refers to a composition having autologous thrombin (AT) and autologous platelets.

A "thrombin composition" refers to a composition having thrombin. In one embodiment of the invention, a thrombin composition is provided that has an extended "table-life."

An "autologous thrombin composition" refers to a composition having thrombin obtained from the same individual (i.e., donor) to whom the composition is to be administered (i.e., recipient).

By "table-life" is meant the period of time during which a component of a composition, such as a protein or substance, may be stored at a given temperature and remain suitable for use, i.e., remain "biologically active." A "biologically active" protein is one having enzymatic activity, mitogenic activity, protein binding activity, and/or a receptor binding activity, as measured or observed in vivo (i.e., in the natural physiological environment of the protein in the organism) or in vitro (i.e., under laboratory conditions, in tissue culture or cell free systems, for example). As an example, thrombin is known to have enzymatic activity, e.g., thrombin converts fibrinogen into fibrin by hydrolyzing peptides (and amides and esters) of L-arginine; as well as mitogenic activity, e.g., it induces platelet aggregation. Thus, thrombin having biological activity is, for example, thrombin that is capable of catalyzing the conversion of fibrinogen into fibrin.

As used herein, the phrase "coagulated mass" is meant to refer to the product of the conversion of soluble fibrinogen to insoluble fibrin, which, under native physiological conditions forms a localized clot (or thrombus) together with platelets that prevents the extravasation of blood components. Thus, a "coagulated mass" has insoluble crosslinked fibrin strands and/or non-crosslinked fibrin strands, i.e., fibrin monomers and/or fibrin polymers, and may include a fibrin clot. A "fibrin clot" refers to a cross-linked fibrin clot, or thrombus, which together with platelets under native physiological conditions prevents the extravasation of blood components.

The phrase "plasma protein" is used interchangeably with the phrases "serum protein" and "blood plasma protein," and refers to a protein found in the blood, e.g., albumin, globulin, blood clotting proteins, etc. A "blood clotting protein" refers to a protein of the coagulation process, such as, but not limited to, fibrinogen, Factor XIII, Factor VIII and von Willebrand factor (vWF), fibrin and thrombin.

As used herein "a" or "an" means one or more, unless specifically indicated to mean only one.

II. The Blood Coagulation Process

Blood coagulation results in the formation of a fibrin clot, i.e., blood clot. Blood coagulation includes clotting cascades, enzymatic processes referred to as the intrinsic pathway and extrinsic pathway (FIG. 1). These pathways each lead to the activation of Factor X, and thereafter join to form a final common pathway resulting in the formation of the cross-linked fibrin clot.

Surfaces, such as negatively charged surfaces, tend to activate the intrinsic pathway, while tissue damage tends to activate the extrinsic pathway. Typically, the intrinsic pathway, also known as the contact activation system, is activated by the adsorption of Factor XII (also known as Hageman factor) onto negatively charged surfaces. The mechanism by which negatively charged surfaces initiate coagulation appears to be autoactivation of Factor XII following its adsorption. Factor XII adsorbs onto a surface by displacing previously bound fibrinogen. High molecular weight kininogen (HMWK; HMW-kininogen), which is noncovalently complexed with Factor XI and prekallikrein, also displaces bound fibrinogen. The ability of HMWK to bind to negatively charged surfaces is due, in part, to its positive charge. It appears that HWMK's main role is to facilitate the localization of Factor XI and prekallikrein at the surface where they can be activated by activated Factor XII. Kallikrein (activated prekallikrein) can exert positive feedback on the system through its ability to activate additional Factor XII, whereas activated Factor XI in the presence of calcium activates Factor IX (also known as Christmas factor).

Activated Factor IX, together with calcium, phospholipids, and Factor VIII, causes the activation of Factor X. Factor VIII is thought to be stabilized by von Willebrand factor (vWF). The final, common pathway starts with activated Factor X, which, in the presence of calcium, phospholipids, and Factor V, converts prothrombin to thrombin. Thrombin, a trypsin-like protease, is responsible for catalyzing the conversion of fibrinogen to fibrin and the subsequent polymerization of fibrin. Two different fibrinopeptides, fibrinopeptide A and fibrinopeptide B, are released from fibrinogen during hydrolytic cleavage of fibrinogen by thrombin. These cleaved fibrinogen molecules, also known as fibrin monomers, then polymerize noncovalently to form insoluble fibrin strands. The covalent crosslinking of the insoluble fibrin strands, also known as ligation, occurs in the presence calcium and activated plasma transglutaminase (also known as Factor XIIIa or fibrin stabilizing factor).

The extrinsic pathway of the coagulation cascade is activated by tissue factor (also known as factor III). Tissue factor, which is typically released into the blood following tissue damage, is an enzymatically inert glycoprotein found on the surface of many cell types. Circulating tissue factor interacts with Factor VII, catalyzing the activation of Factor X, thereby joining the common pathway.

As discussed above, fibrinogen is converted into fibrin by thrombin, a proteolytic enzyme. Fibrinogen is made up of three pairs of polypeptides $([A-\alpha][B-\beta][\gamma])_2$. The six chains are covalently linked near their N-terminals through disulfide bonds. The A and B portions of the A-$\alpha$ and B-$\beta$ chains comprise the fibrinopeptides, A and B, respectively. The fibrinopeptide regions of fibrinogen contain several glutamate and aspatate residues imparting a high negative charge to this region and aid in the solubility of fibrinogen in plasma. Active thrombin, a serine protease, hydrolyses fibrinogen at four arginine-glycine peptide bonds to release an A peptide (fibrinopeptide A) from each of the two $\alpha$ chains and a B peptide (fibrinopeptide B) from each of the two $\beta$ chains. A fibrinogen molecule devoid of these fibrinopeptides is referred to as a fibrin monomer, represented by $(\alpha\beta\gamma)_2$. These fibrin monomers spontaneously aggregate in ordered fibrous arrays referred to as fibrin polymers, which form a weak fibrin clot. The clot produced by the spontaneous aggregation of fibrin monomers is stabilized by the formation of covalent cross-links between the side chains of different molecules in the fibrin fiber. In particular, thrombin converts Factor XIII to Factor XIIIa, a highly specific transglutaminase that forms peptide bonds between the amide nitrogen of glutamines and e-amino group of lysines in the fibrin monomers, resulting in a cross-linked fibrin clot.

III. Anticoagulants of the Present Invention

Certain embodiments of the methods of the present invention begin with anticoagulated whole blood, which may be prepared by collecting whole blood in a medium containing an anticoagulant, such as sodium citrate (citrate). The act of drawing blood initiates clotting reactions, and, unless something is done to stop the process, a clot generally forms. The formation of a clot is a multi-step process, as described above, and several of these steps require the presence of calcium ions. By removing calcium ions from the whole blood, as is the effect when the blood is collected in citrate, the blood may be prevented from clotting. To reinitiate the clot-forming process, calcium may be added back (recalcification). A calcium chelating agent is a chemical that reacts with the calcium present in blood in such a fashion so as to prevent calcium from functioning in blood coagulation. The most common chelating agent is a salt of citric acid (citrate), since it has the fewest side effects on the components of the coagulation system. By collecting blood into a medium containing a calcium chelating agent such as citrate, sample collection and further preparations of the citrated sample may be performed over a time period of up to several hours.

In one embodiment, whole blood may be collected and mixed with a solution of sodium citrate, e.g., 3.8%, in a 9:1 ratio of blood to citrate collection medium. A 3.8% solution of sodium citrate may be prepared by adding 3.8 grams of sodium citrate per 100 ml of water. While a 3.8% solution of sodium citrate may be used to collect and preserve blood, the person skilled in this art will recognize that the ratio of sodium citrate to whole blood can vary greatly. For example, the ratio of sodium citrate to whole blood may be in the range of about 10.9 to greater than 12.9% mM/L, final concentration.

Alternatively, or in addition to, one or more anticoagulants such as heparin, heparin derivatives and/or heparin-like substances, may be used to form or to help form an anticoagulated whole blood sample. Heparin, a sulphated glycosaminoglycan, is known to inhibit blood coagulation by binding to antithrombin III (ATIII), a serine protease inhibitor (serpin) found in blood. The binding of heparin to ATIII enhances the activity of the serpin, which, in turn, inactivates the procoagulant serine proteins thrombin, Factor Xa and, to some extent, Factors IXa, XIa, and XIIa. Heparin accelerates the reactions of ATIII with the blood-clotting proteases from ~1,000 to ~10.000-fold.

Alternatively, or in addition to, one or more anticoagulants such as hirudin, recombinant hirudin, e.g., desirudin, hirulogs, hirudin analogs, e.g., angiomax (bivalirudin) and/or lepirudin, may be used to form or to help form an anticoagulated whole blood sample. Hirudin is a direct acting thrombin inhibitor.

Alternatively, or in addition to, one or more synthetic thrombin inhibitors, such as argatroban (novastan) and PPACK (dextrophenylalanine proline arginine chloromethylketone), and Xa inhibitors may be used to form or to help form an anticoagulated whole blood sample.

IV. Clotting Activators of the Present Invention

One or more coagulation or clotting activators may be used to hasten or accelerate one or more steps of the coagulation process; however, their subsequent removal may be necessary. The phrase "clotting activator" is used interchangeably herein with the phrase "coagulation activator" and refers to an agent that participates in the coagulation process, e.g., an agent that initiates the intrinsic coagulation pathway, the extrinsic coagulation pathway, or both. Examples of clotting activators include, but are not limited to, collagen, celite, contact activation agents and extrinsic coagulation pathway initiation agents. By "contact activation agent" is meant an agent involved in the intrinsic pathway of coagulation, and includes but is not limited to glass, glass beads, diatomaceous earth, ceramics, kaolin, and any combination thereof. By "extrinsic coagulation pathway initiation agent" is meant an agent involved in the extrinsic pathway of coagulation, and includes but is not limited to tissue factor (TF), thromboplastin, factor III, tissue thromboplastin and/or recombinant thromboplastin, as well as thrombin. In addition, other compounds may be used alone or in combination with other activating compounds or contact activators. In addition, compounds such as recombinant thromboplastin, tissue thromboplastin (human or animal), tissue factor fragments, epinephrine, adenosine diphosphate (ADP), thrombin receptor activating peptides (TRAPs), arachidonic acid, collagen, and/or combinations thereof may be used as a clotting activator in the methods of the present invention.

Additionally, physical or mechanical manipulation of the platelet membrane may be used alone or in combination to speed up the clotting process. Mechanical forces may be, for example, liquid, gas or solid in nature.

V. Restoration Agents of the Present Invention

A restoration agent, i.e., an agent capable of reversing or neutralizing the effects of an anticoagulant, may be used in the present invention to restore one or more steps of the coagulation or clot-forming process. In one embodiment, the restoration agent comprises a source of calcium ions, e.g., a calcium salt such as calcium chloride or calcium gluconate. Any calcium salt that reverses or neutralizes the anticoagulant may be used as a source for calcium ions in the methods described herein. For example, organic or inorganic salts may be used as long as they can transfer $Ca^{++}$ to serum proteins. Suitable organic calcium salts include calcium propionate and calcium acetate. Suitable inorganic salts include calcium hydroxide, calcium ammoniate, calcium carbide, calcium carbonate, calcium sulfate, calcium nitrate, and calcium pyrophosphate. Substances that are known or found to be functionally equivalent to calcium chloride in restoring the coagulation activity of citrated blood may also be used. For example, any calcium salt that functions in a similar manner to calcium chloride may be used. Similarly, although many blood coagulation reactions require calcium ions as cofactors, any substance that is known or subsequently found to be functionally equivalent to calcium in facilitating these coagulation reactions may be used, either individually or in combination with calcium, in the practice of the present invention.

Alternatively, if the anticoagulant used was heparin, then heparinase or protamine, for example, may be used as a restoration agent to reverse or neutralize the effects of the anticoagulant. The concentrations of one or more restoration agents used to reverse the effects caused by one or more anticoagulation agents will depend in part, upon the concentrations of the one or more anticoagulation agents present in the plasma, e.g., PPP and/or PRP, and the stoichiometry of the chelating and coagulation reactions. In one embodiment of the present invention, the concentrations of the one or more restoration agents used to reverse the one or more anticoagulation agents must be sufficient to achieve clot formation.

In one embodiment of the present invention, one or more restoration agents and/or one or more coagulation activators may be used alone or in combination to restore and/or accelerate one or more steps of the coagulation process. In certain embodiments, restoration agent may also be a coagulation activator.

VI. Protecting Groups of the Present Invention

In one embodiment of the present invention, one or more protecting groups may be used to protect one or more functional groups of one or more substances being isolated and/or concentrated. For example, carbonyl protecting groups include the formation of cyclic acetals. For example, a carbonyl functional compound or substance of interest may be protected by reaction with 1,2-ethanediol or propane-1,3-diol in the presence of an acid catalyst. The cyclic acetal may be removed when desired in the presence of aqueous acid. Alcohol protecting groups include the formation of acetals, ethers and trialkyl silyl ethers, for example. A hydroxyl functional compound or substance of interest may be protected by reaction with silyl chloride in the presence of a mild base, such as imidazole. Amine protecting groups include the formation of amides or carbamates, for example. Amine protecting groups include the formation of N-acyl derivatives and N-sulfonyl derivatives, for example. A primary amine functional coumpound or substance may be protected by the reaction with phthalic anhydride.

VII. Recombinant Proteins of the Present Invention

One or more recombinant proteins and/or substances may be used in the methods of the present invention. For example, recombinant human fibrinogen (rhFg), recombinant thrombin (rhThr) or other clotting proteins and/or factors may be employed. Recombinant proteins possess the same molecular structure as their naturally occurring counterparts, but are produced in non-human systems such as bacteria, yeast, cultured animal cells or even whole animals. These surrogate systems may be induced to produce the protein of interest in high quantities under controlled conditions. This may be accomplished by transferring an isolated human gene into the host organism.

Recombinant proteins may be readily available for use in biological compositions, e.g., a fibrin composition or a thrombin composition, since they are generally stored as dry powders (lyophilized) at room temperature or colder. In one embodiment of the present invention, one or more lyophilized proteins and/or substances may be resuspended in an appropriate solvent (e.g., PRP and/or PPP). In addition, the ability to store powdered forms of the recombinant proteins and/or substances increases their stability.

For example, recombinant fibrinogen and/or other clotting proteins such as factor VIII or factor XIII may be added to either PRP and/or PPP in order to increase the fibrin network created upon formation of a gel or coagulated mass. In one embodiment, recombinant thrombin may be solubilized or dissolved in a calcium chloride solution, for example, if sodium citrate was used as the anticoagulant, in order to form the fibrin composition at the site of action.

PRP and PPP, e.g., autologous PRP and PPP, may be prepared from whole blood, as described herein. Recombinant thrombin may be mixed with the PRP and/or PPP and optionally with recombinant fibrinogen to create a "customizable" fibrin composition. For example, autologous PRP may be combined with recombinant fibrinogen and recombinant thrombin to form a platelet rich fibrin composition useful for hemostatis, sealing and wound healing. Autologous PRP may be combined with recombinant thrombin to create an autologous platelet gel (APG) composition useful for hemostasis and wound healing. In addition, autologous PPP may be combined with recombinant fibrinogen and recombinant thrombin to create a fibrin composition useful for hemostasis and sealing.

VIII. Stabilizing Agents of the Present Invention

One or more stabilizing agents, i.e., an agent capable of prolonging the "life" of a protein and/or substance present in one of the compositions of the invention, may be used to prolong the "table-life" of one or more proteins and/or substances in one or more components of a biological composition. By "table-life" is meant the period of time during which the proteins and/or substance may be stored at a given temperature and remain suitable for use, e.g., remain "biologically active." As used herein, a "biologically active" protein or substance exhibits an activity such as, for example, an enzymatic activity, a mitogenic activity, a protein binding activity, and/or a receptor binding activity, as measured or observed in vivo (i.e., in the natural physiological environment of the protein or substance in the organism) or in vitro (i.e., under laboratory conditions, in tissue culture or cell free systems, for example). As an example, thrombin is known to have a variety of biological activities, such enzymatic activity, e.g., thrombin converts fibrinogen into fibrin, e.g., by hydrolyzing peptides (and amides and esters) of L-arginine; as well as mitogenic activity, e.g., it induces platelet aggregation. Thus, thrombin having biological activity is, for example, thrombin that may catalyze the conversion of fibrinogen into fibrin.

Exemplary stabilizing agents include, but are not limited to polyols, e.g., glycerol; PEG; ammonium sulfate; non-polar solvents such as chloroform and the like; polar solvents such as ethanol, methanol, isopropanol, n-propanol, cyclohexanol, acetone, DMSO, and the like; methyl isobutyl ketone alcohols; glycols; tricloroacetic acid; acetate salt; and/or combinations thereof may be used. In one embodiment, temperature, e.g., temperatures colder than physiological temperature may be used as an "agent" to stabilize one or more proteins and/or substances.

Any agent that binds or otherwise renders proteins and/or substances that contribute to the degradation of thrombin "unavailable" may be used as a stabilizing agent. Any agent that preserves thrombin and/or prevents the denaturation of thrombin, i.e., maintains or improves the activity of thrombin may be used as a stabilizing agent. Stabilizing agents include, for example, agents that prevent the autolytic degradation and/or denaturation of thrombin; agents that remove and/or inhibit the negative regulators of coagulation such as antithrombin III, tissue factor pathway inhibitor (TFPI), and/or components of the protein C system (protein C, protein S and thrombomodulin).

In one embodiment of the methods described herein of the present invention, ethanol may be used as a thrombin stabilizing agent. The addition of ethanol to a thrombin preparation can precipitate antithrombin III (ATIII) (via ethanol fractionation), thus reducing ATIII's inhibitory function in the intrinsic coagulation pathway for the catalysis of prothrombin to thrombin. In certain embodiments, ethanol in the range of about 8% to about 25% (vol/vol) may be used as a stabilizing agent to provide a thrombin composition having a table-life of more than about six hours.

While not intending to be bound to any particular theory regarding the mechanism of action, it is believed that the carboxylic group of the thrombin reacts with the hydroxyl group of the alcohol forming an ester, thus preventing the autolytic degradation of thrombin. In addition or alternatively, it is believed that the presence of an organic solvent affects protein folding, which in turn affects the activity of thrombin, an effect that may not be permanent. Again, not wishing to be bound by theory, when a thrombin composition comprising an organic solvent is combined with a blood plasma component, such as platelet rich plasma, platelet poor plasma, etc., the concentration of the organic solvent decreases, this in turn can increase the activity of thrombin. Thus, the organic solvent may act as a "switch," controlling the activity of thrombin. In addition, or as an alternative, the stabilizing agents, for example, as described herein, may denature and thus 'remove' proteins that inactivate thrombin, e.g., antithrombin III. Protein C (and protein S) typically regulates the formation of thrombin under normal, physiologic conditions. While not being bound by theory, the stabilizing agents may denature and effectively 'remove' Protein C (and Protein S), thus allowing any remaining prothrombin to be converted into thrombin. Therefore, thrombin concentrations may increase after the addition of one or more stabilizing agents as discussed herein.

In one embodiment of the present invention, cold temperatures may be used to inhibit and/or prevent the degradation of one or more proteins and/or substances of the biological compositions described herein. In certain embodiments, cold temperatures can minimize degradation of one or more proteins and/or substances of the composition without negatively affecting performance, e.g., biological activity, when the composition is warmed just prior to forming the fibrin composition, e.g., a platelet rich fibrin composition. In one embodiment, temperatures colder than physiological temperature can inhibit and/or prevent autocatalytic activity of thrombin, and are used to stabilize thrombin preparations prepared according to one or more the methods of the present invention.

IX. Additional Agents Useful in the Compositions and Methods of the Present Invention In one embodiment of the present invention, recombinant human agents or substances, e.g., proteins and/or enzymes, may be used to form a biological composition, e.g., recombinant human thrombin and/or recombinant human fibrinogen may be used. In an alternative embodiment of the present invention, agents or substances, e.g., proteins and/or enzymes, from a non-human source may be used to form a biological composition, e.g., bovine or porcine thrombin and/or bovine or porcine fibrinogen may be used. In yet another embodiment, a complete recombinant mixture of proteins in buffer and recombinant thrombin may be used to generate a biological composition. For example, recombinant thrombin, one or more recombinant proteins, e.g., recombinant fibrinogen, PPP may be mixed together to form a fibrin composition according to one embodiment of the present invention. If the composition comprises fibrinogen, then the fibrin composition may be used, for example, as a fibrin sealant composition.

In one embodiment of the present invention, one or more anticoagulants, clotting activators, restoration agents and/or stabilizing agents, as described herein, may be used in the method of making a biological composition, e.g., a fibrin composition.

In one embodiment of the present invention, a biological composition, e.g., a fibrin composition, of the present invention may be used as a delivery vehicle for one or more agents or substances including pharmaceutical agents, therapeutic agents, medical agents and/or biological agents. Agents that may be added to a fibrin composition of the present invention may be found in nature (naturally occurring) or may be chemically synthesized by a variety of methods well known in the art. One or more components of a fibrin composition including agents that may be added to the fibrin composition may be derived from humans and/or animals and/or they may be derived from various recombinant techniques.

A fibrin composition of the present invention may include one or more agents or substances described herein, or any substance suitable for providing a desired effect, e.g., a biological effect, a chemical effect, a mechanical effect, an electrical effect and/or a physiological effect. In one embodiment of the present invention, it is envisioned that selected fragments, portions, derivatives, or analogues of one or more of the pharmaceutical agents, therapeutic agents, medical agents and/or biological agents may be added to a fibrin composition of the present invention. Examples of pharmaceutical agents, therapeutic agents, medical agents and/or biological agents that may be added to a fibrin composition of the present invention include, but are not limited to, drugs, anticoagulant agents, antithrombotic agents, including heparin, heparin derivatives, hirudin, and PPACK (dextrophenylalanine proline arginine chloromethylketone), thrombolytic agents including urokinase and/or tissue type plasminogen activator, clotting agents, platelet agents, antibodies, antigens, defense agents, growth factors, neurotransmitters, cytokines, blood agents, tissue agents, regulatory agents, transport agents, fibrous agents, proteoglycans, hyaluronic acid, fatty acids, analgesic agents, anesthetic agents, including lidocaine, bupivacaine, and ropivacaine, antimicrobial agents, including triclosan, cephalosporins, aminoglycosides, and nitorfurantoin, antibacterial agents, including bacteriocidal and bacteriostatic agents, bacterial agents, antibiotic agents, including adriamycin, erythromycin, gentamycin, vancomycin, penicillin, tobramycin, antifungal agents, antiparasitic agents, antiviral agents, viral agents, enzymes, enzyme inhibitors, glycoproteins, growth factors, lymphokines, cytokines, hormones, steroids, glucocorticosteroids, immunomodulators, immunoglobulins, minerals, neuroleptics, carbohydrates, polysaccharides, amino acids, proteins, peptides, polypeptides, lipoproteins, tumoricidal compounds, tumorstatic agents, toxins, vitamins, including Vitamin A, Vitamin E, Vitamin B, Vitamin C, Vitamin D, or derivatives thereof, oligonucleotides, ribozymes, genetic agents, anti-sense gene agents, DNA segments, RNA segments, DNA compacting agents, gene/vector systems, nucleic acids, including recombinant nucleic acids, naked DNA, cDNA, RNA, genomic DNA, cDNA, RNA in a non-infectious vector or in a viral vector which may have attached peptide targeting sequences, antisense nucleic acid (RNA or DNA), and DNA chimeras which include gene sequences and encoding for ferry proteins such as membrane translocating sequences ("MTS") and herpes simplex virus-1 ("VP22"), liposomes, ionic agents, cationic agents, anionic agents, monomers, polymers, catalysts, lectins, ligands, dyes, including dyes which act as biological ligands, antioxidants, including probucol and retinoic acid, angiogenic agents, anti-angiogenic agents, agents that block smooth muscle cell proliferation, including rapamycin, angiopeptin, and monoclonal antibodies capable of blocking smooth muscle cell proliferation, anti-inflammatory agents, including dexamethasone, prednisolone, corticosterone, budesonide, estrogen, sulfasalazine, acetyl salicylic acid, and mesalamine, calcium entry blockers, including verapamil, diltiazem and nifedipine, antineoplastic agents, antiproliferative agents, anti-mitotic agents, including paclitaxel, 5-fluorouracil, methotrexate, doxorubicin, daunorubicin, cyclosporine, cisplatin, vinblastine, vincristine, epothilones, endostatin, angiostatin and thymidine kinase inhibitors, nitric oxide (NO) donor agents, including lisidomine, molsidominc, L-arginine, NO-protein adducts, NO-carbohydrate adducts, polymeric or oligomeric NO adducts, an RGD peptide-containing agent, anti-thrombin agents, platelet receptor antagonists, anti-thrombin antibodies, anti-platelet receptor antibodies, enoxaparin, Warafin sodium, Dicumarol, aspirin, prostaglandin inhibitors, platelet inhibitors and tick antiplatelet factors, vascular cell growth promoters, including growth factors, growth factor receptor antagonists, transcriptional activators, and translational promoters, vascular cell growth inhibitors, including growth factor inhibitors, growth factor receptor antagonists, transcriptional repressors, translational repressors, replication inhibitors, inhibitory antibodies, antibodies directed against growth factors, bifunctional molecules consisting of a growth factor and a cytotoxin, bifunctional molecules consisting of an antibody and a cytotoxin, cholesterol-lowering agents, vasodilating agents; agents which interfere with endogenous vasoactive mechanisms, survival genes which protect against cell death, including anti-apoptotic Bcl-2 family factors and Akt kinase, and combinations thereof.

Examples of polynucleotide sequences that may be used in one embodiment of the present invention include DNA or RNA sequences having a therapeutic effect after being taken up by a cell. Examples of therapeutic polynucleotide agents include anti-sense DNA and RNA; DNA coding for an anti-sense RNA; or DNA coding for tRNA or rRNA to replace defective or deficient endogenous molecules. The polynucleotide agents of one embodiment of the present invention may also code for therapeutic proteins or polypeptides. A polypeptide may be a translation product of a polynucleotide regardless of size, and whether glycosylated or not. Therapeutic proteins and polypeptides according to one embodiment of the present invention may include those proteins or polypeptides that can compensate for defective or deficient species in an animal, or those that act through toxic effects to limit or remove harmful cells from the body, for example. In addition, the polypeptides or proteins useful in one embodiment of the present invention may include, without limitation, angiogenic factors and other molecules competent to induce angiogenesis, including acidic and basic fibroblast growth factors, vascular endothelial growth factor, hif-1α, FGF-1, FGF-2, IGF, epidermal growth factor, transforming growth factor alpha and beta, platelet-derived endothelial growth factor, platelet-derived growth factor, tumor necrosis factor alpha, hepatocyte growth factor and insulin like growth factor, growth factors, cell cycle inhibitors including CDK inhibitors, anti-restenosis agents, including p15, p16, p18, p19, p21, p27, p53, p57, Rb, nFkB and E2F decoys, thymidine kinase ("TK") and combinations thereof and other agents useful for interfering with cell proliferation, including agents for treating malignancies and combinations thereof. Still other useful agents or factors that may be used in one embodiment of the present invention, which may be provided as polypeptides or as DNA encoding these polypeptides, include monocyte chemoattractant protein ("MCP-1"), and the family of bone morphogenic proteins ("BMP's"), including BMP-2, BMP-3, BMP-4, BMP-5, BMP-6 (Vgr-1), BMP-7 (OP-1), BMP-8, BMP-9, BMP-10, BMP-11, BMP-12, BMP-13, BMP-14, BMP-15, and BMP-16. For example, BMP's such as BMP-2, BMP-3, BMP-4, BMP-5, BMP-6 and/or BMP-7 may be used. These dimeric proteins can be provided as homodimers, heterodimers, or combinations thereof, alone or together with other molecules. Alternatively or, in addition, agents capable of inducing an upstream or downstream effect of a BMP may be used. Such agents may include any of the "hedgehog" proteins, or the DNA's encoding them.

In one embodiment of the present invention, micro-particles, e.g., biodegradable micro-particles, may be added to a fibrin composition of the present invention. For example, micro-particles small enough for injection through a needle but too large to fit into capillaries and venules, may be added to a fibrin composition. In one embodiment, the micro-particles may be impregnated with one or more pharmaceutical agents, therapeutic agents, medical agents and/or biological agents that can elute, e.g., as the micro-particles degrade.

In one embodiment of the present invention, a fibrin composition may include one or more chemicals, e.g., polymers and/or chemical cross-linkers, that may chemically bind to one or more chemical constituents, e.g., proteins, located within tissue. For example, one or more proteins that can chemically bind to the surface of one or more cell types contained in tissue may be used according to one embodiment. In one embodiment, polymers that can covalently bind to primary amine groups ($-NH_3$) of proteins contained within target tissue may be used. Several embodiments of a fibrin composition may include pro-inflammatory molecules, such as histamine, cytokines, and/or chemokines. At least one embodiment of a fibrin composition of the present invention may include one or more contrast agents that may be for visual identification of the fibrin composition. Examples of contrast agents include, but are not limited to, X-ray contrast (e.g., IsoVue), MRI contrast (e.g., gadolinium), and ultrasound contrast (e.g., echogenic or echo-opaque compounds).

In one embodiment of the present invention, one or more cells or cell types may be added to a fibrin composition of the present invention. For example, cells such as bone marrow cells, stem cells, mesenchymal stem cells, pluripotent cells, myocytes, cardiocyte precursor cells, undifferentiated contractile cells and/or cells capable of maturing into actively contracting cardiac muscle cells may be added to a fibrin composition of the present invention. Typically, undifferentiated contractile cells differentiate to form muscle cells, however, they can be fibroblasts that have been converted to myoblasts ex vivo, or any of a wide variety of immunologically neutral cells that have been programmed to function as undifferentiated contractile cells. Cells of mesodermal origin that form contractile cells may be added to a fibrin composition of the present invention, and include skeletal muscle cells, heart muscle cells, and smooth muscle cells, as well as precursor cells to the cells, such as pluripotent stem cells, embryonic stem cells, mesodermal stem cells, myoblasts, fibroblasts, and cardiomyocytes. Suitable cells for use in the present invention may include umbilical cells and skeletal muscle satellite cells. Suitable cells for use in the present invention may also include differentiated cardiac or skeletal cells, such as cardiomyocytes, myotubes and muscle fiber cells, and the like. Cells that may be used according to one or more embodiments of the present invention may be autologous, allogeneic or xenogenic, genetically engineered or non-engineered. Mixtures of various cell types may be used. Cells capable of establishing healthy tissue in damaged or diseased tissue areas or cells aiding in the angiogenesis process may be used according to one or more embodiments of the present invention.

One embodiment of the present invention enables one or more agents, substances and/or components, as described earlier, to be added or mixed prior to delivery by one or more delivery devices. For example, in one embodiment of the present invention, one or more agents or substances as described herein may be added to the thrombin, PPP and/or PRP and protein mixture prior to delivery of a fibrin composition to a patient. Alternatively, in one embodiment of the present invention, one or more agents or substances as described herein, for example, may be added to the thrombin component prior to mixing the thrombin, PPP and/or PRP and protein components together. Alternatively, in one embodiment of the present invention, one or more agents or substances as described herein, for example, may be added to the PPP and/or PRP components prior to mixing the thrombin, PPP and/or PRP and protein components together. Alternatively, in one embodiment of the present invention, one or more agents or substances as described above, for example, may be added to the protein component prior to mixing the thrombin, PPP and/or PRP and protein components together.

X. Thrombin Compositions of the Present Invention

In one embodiment, the present invention provides a method for preparing a thrombin composition, for example, an autologous thrombin (AT) composition. For example, an AT composition can be prepared by extracting thrombin from whole blood, e.g., anticoagulated whole blood, a component thereof such as blood plasma and/or a fraction thereof such as platelet poor plasma, platelet rich plasma, and the like, that is obtained from a subject to whom the thrombin composition is to be administered, i.e., the recipient of the composition.

As discussed above, thrombin is a serine protease that proteolytically cleaves fibrinogen to form fibrin, which is ultimately integrated into a crosslinked network. In certain embodiments of the present invention, the process begins upon restoration of the whole blood, component thereof or fraction thereof, such as PRP and/or PPP. In one embodiment, this results in a "coagulated mass," which as referred to herein includes both insoluble crosslinked fibrin strands and/or non-crosslinked fibrin strands. According to the methods provided herein, the time it takes to form the coagulated mass, i.e., the "coagulation time," also referred to as clotting time and/or blood clotting time, may be reduced as compared to conventional thrombin preparation techniques. Once formed, the coagulated mass is triturated by high speed centrifugation or squeezed through a mesh to provide serum containing thrombin. The thrombin may then be used, for example, to prepare a fibrin composition according to at least one method disclosed herein In another embodiment, thrombin is obtained from a coagulated mass prepared by contacting a source of thrombin and a source of fibrinogen with a contact activation agent(s), extrinsic coagulation pathway initiation agent(s) or combination thereof. As discussed infra, the blood coagulation process, also known as the coagulation cascade, can be activated through either the extrinsic or intrinsic pathway. These enzymatic pathways share one final common pathway, resulting in formation of a crosslinked fibrin clot. The first step of the common pathway of the coagulation cascade involves the proteolytic cleavage of prothrombin by the Factor Xa/Factor Va prothrombinase complex to yield active thrombin.

It has been discovered by the present inventors that the presence of ethanol during the production of thrombin from whole blood, a component thereof or a fraction thereof, such as PRP and/or PPP, increases (slows down) the plasma clotting time. Thus, in one embodiment of the present invention, ethanol is not present during the production of thrombin. When ethanol is not present, for example, as a chemical precipitation agent, during the processing of blood into fibrinogen and/or thrombin, the time it takes to form a coagulated mass can be reduced from about 30 minutes at room temperature to in the range of about 2 minutes to about 4 minutes at room temperature. In addition, in certain embodiments of the methods, thromboplastin is used to accelerate plasma clotting time.

A stabilizing agent, for example, ethanol and/or a reduced temperature, may be used to prolong the "table-life" of a thrombin composition made according to the methods described herein. The addition of a stabilizing agent(s) to a thrombin composition may provide a thrombin composition having a biological activity of more than 6 hours, for example, about 12 hours or up to about 24 hours. The thrombin in such a composition has a biological activity, e.g., enzymatic activity, for more than 6 hours when stored at room temperature. For example, a thrombin composition prepared according to the present invention may be used in combination with a source of fibrinogen to form a fibrin composition that "gels" or forms a cross-linked fibrin clot in about 5 seconds or less after having been stored for about 6 hours or more at room temperature. In another embodiment, a thrombin composition prepared according to the present invention may be used in combination with a source of fibrinogen to form a fibrin sealant composition in about ten seconds or less.

Assays for determining thrombin activity are known to the art and include, e.g., amidolytic assays, clotting assays, etc. In addition, in vitro analysis of the biological activity of thrombin may be conducted using a chromogenic substrate measured spectrophotometrically. Using stabilizing agents according to the methods of the present invention may extend the table-life of a thrombin preparation. Thus, by the addition of a stabilizing agent to the thrombin preparation, the table-life of thrombin may be extended, for example, by 3 or more hours. In certain embodiments of the methods disclosed herein, a stabilizing agent(s) is added to a thrombin preparation once thrombin is extracted or isolated from whole blood, blood plasma or a fraction or component thereof such as platelet rich plasma, platelet poor plasma, to provide a thrombin composition PRP and/or PPP, or a combination or fraction thereof.

XI. Centrifugation

As shown in FIGS. 2-7, whole blood, e.g., anticoagulated whole blood, a component thereof, e.g., thrombin, or a fraction thereof, e.g., plasma, PPP or PRP, is fractionated, e.g., centrifuged, in certain embodiments of the present invention. For example, anticoagulated whole blood is centrifuged using the Medtronic Magellang autologous platelet separator to form platelet rich plasma (PRP) and/or platelet poor plasma (PPP) (FIGS. 2-7). In one embodiment of the present invention, anticoagulated whole blood is centrifuged at a rate of approximately 200-800 r.c.f.'s for about 4 to about 40 minutes to provide two liquid phases.

In certain embodiments, centrifugation occurs at refrigerated temperatures. For example, anticoagulated whole blood is centrifuged at refrigerated temperatures and 600 r.c.f.'s for about 4 minutes to provide two liquid phases, e.g., a top PRP phase, and a bottom phase that is anticoagulated whole blood minus the platelet rich plasma. The PRP is then gently drawn off and saved in a first container. The PRP phase may be further centrifuged, e.g., at a rate of approximately 1000-2000 r.c.f.'s for about 3 to about 12 minutes. In one embodiment, the PRP phase is centrifuged at refrigerated temperatures and 1200 r.c.f.'s for about 3 to about 6 minutes. This higher rate of centrifugation results in the red blood cells, white blood cells and platelets being spun out of the PRP phase, thereby further concentrating the cellular components. The resulting PPP, following removal of the concentrated cellular components, is then saved in a second container.

The first container, second container or both, may have either a wettable surface (such as silica, diatemaceous earth, kaolin, etc.) or a non-wettable surface (such as plastic, siliconized glass, etc.). Because surfaces play a role in activating blood coagulation, the choice of surface for either the first or second container is dependent on whether or not clot formation and/or the activation of one or more steps of the coagulation process is desired. In one embodiment, a plastic syringe may be used to collect the PRP and/or the PPP.

In one embodiment of the present invention, the PRP may include plasma with an above-normal amount of platelets. In another embodiment, the PRP may include plasma, platelets, white blood cells, or a combination thereof. In yet another embodiment, the PRP may include additional components, e.g., red blood cells. In yet another embodiment, the PRP includes a higher concentration of platelets than the starting sample, e.g., the anticoagulated whole blood sample.

In one embodiment of the present invention, the PPP may include plasma with a below-normal amount of platelets, e.g., plasma that is free of platelets and/or plasma free of white blood cells. In another embodiment, fresh frozen plasma may be substituted for PPP. In yet another embodiment, the PPP may include additional components, e.g., red blood cells. In yet another embodiment, the PPP includes a lower concentration of platelets than the starting sample, e.g., the anticoagulated whole blood sample.

Figure 7:
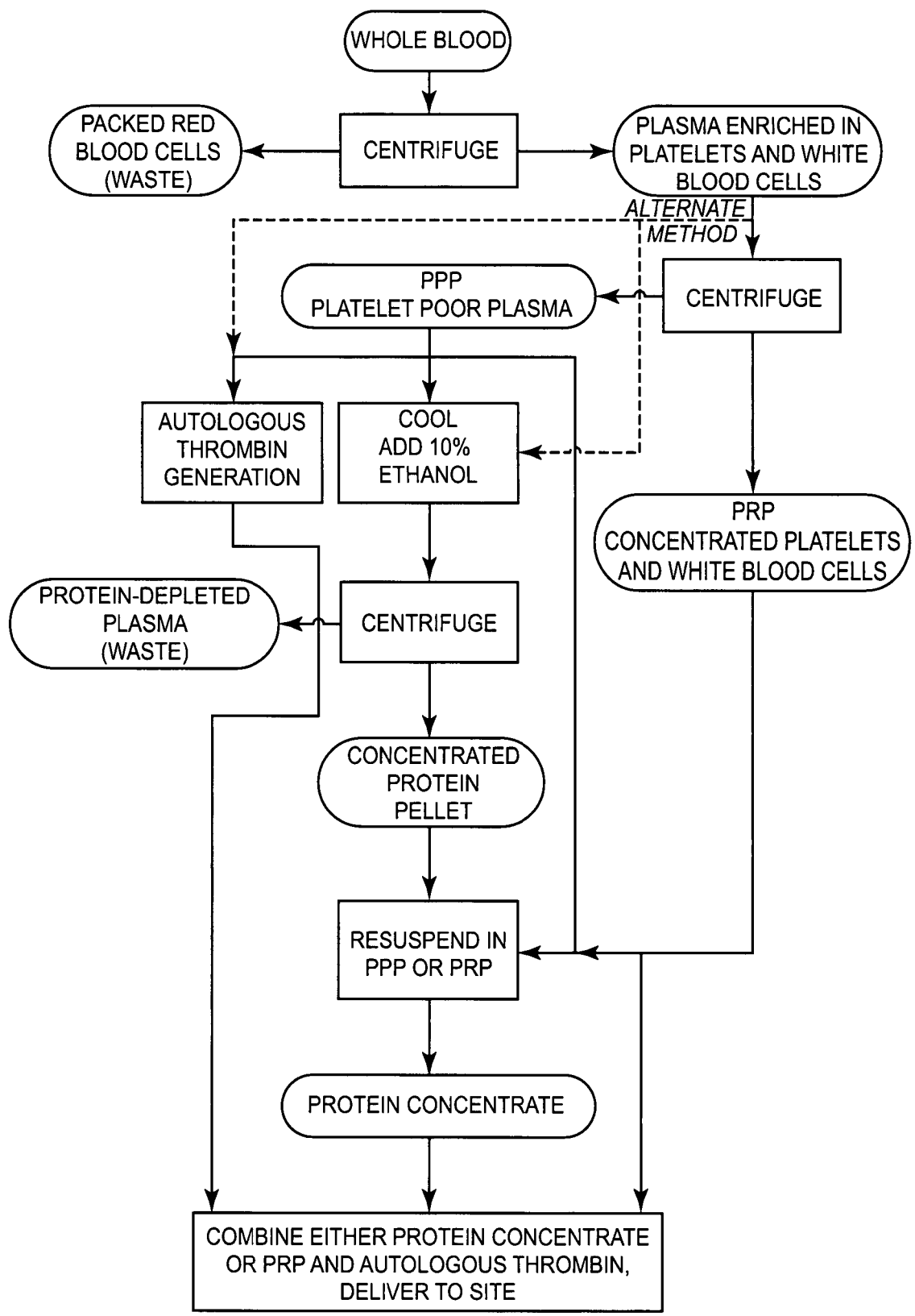
FIG. 7 is a flow diagram of one embodiment in accordance with the present invention.

In another embodiment, PPP prepared from whole blood as described above, then cooled and further centrifuged at refrigeration so as to provide a protein concentrate, e.g., plasma having concentrated fibrinogen and other blood coagulation proteins. In one such embodiment, for example, as shown in FIG. 7, PPP is contacted with 10% ethanol prior to refrigerated centrifugation.

XII. Methods of Concentrating Plasma Proteins

The fibrin compositions and/or thrombin compositions of the present invention can be prepared by fractionating whole blood, removing cellular components, and then applying various methods to isolate fibrin and/or thrombin from the resulting blood plasma fractions. Alternatively, the fibrin compositions and/or thrombin compositions may be prepared directly from whole blood. Methods such as cryoprecipitation, physico-chemical precipitation, the use of micro-filter technology, density gradient technology, dialysis, chromatography, electrophoresis and dehydration and the like may be used, for example, to isolate and/or concentrate one or more components used in the preparation of a biological composition, e.g., a fibrin composition. In one embodiment of the present invention, one or more clotting proteins, e.g., fibrinogen, Factor VIII and Factor XIII, may be isolated and/or concentrated, for example, from a blood plasma fraction. In one embodiment of the present invention, fibrinogen concentration in a biological composition of the present invention is greater than about 3 times the normal fibrinogen concentration in whole blood and/or plasma.

A. Cryoprecipitation

As discussed above, in one embodiment of the present invention a fraction of whole blood, i.e., PPP, is centrifuged at refrigerated temperature with ethanol to concentrate PPP. Thus, cryoprecipitation can be used in the methods of the invention to concentrate proteins, such as clotting proteins that are present in whole blood, a fraction thereof or a component thereof. Cryoprecipitation methods are known in the art, see for example U.S. Pat. Nos. 4,928,603 and 4,627,879.

In one embodiment, PPP and/or PRP may be frozen, e.g., at a temperature below 0° C. such as −80° C., for about 1.5 to 12 hours. Then, the frozen PPP and/or PRP is slowly thawed to provide an insoluble protein precipitate that can then be collected by centrifugation, e.g., at approximately 1000 r.c.f's for approximately 15 minutes. For example, frozen PPP is controllably thawed at about 1 to about 4° C. for approximately about 2 to about 10 hours. The sample is then centrifuged for approximately 10 to 15 minutes at approximately about 1 to 4° C. to separate precipitated proteins. The supernatant is then removed. The precipitated and centrifuged pellet of concentrated proteins is then resuspended at a temperature greater than 6° C. using either a portion of the supernatant or other solvent. The amount of solvent used to resuspend the protein will determine its final concentration. For example, in one embodiment of the present invention, the precipitated and centrifuged pellet of concentrated proteins is resuspended in plasma at a temperature of approximately about 22 to 37° C. In one embodiment, fibrinogen, e.g., autologous fibrinogen, is obtained from a sample of whole blood via cryoprecipitation and added to a platelet gel, e.g., an autologous platelet gel, which results in a platelet gel having enhanced mechanical properties, e.g., enhanced mechanical strength, as well as enhanced clotting time.

B. Chemical Precipitation

Using chemical precipitation methods, certain blood proteins or substances may be precipitated while others are partially precipitated or remain in solution using organic reagents such as ethanol, isopropanol, and/or polyethylene glycol (PEG). Additional precipitation agents include inorganic salts or salt solutions, including but not limited to ammonium sulfate, methanol, glycol, glycine, acetone, cyclohexanol, chloroform, tricloroacetic acid, acetate salt and/or combinations thereof. See, for example, U.S. Patent application publication Nos. 20040120942 and 20040208786; U.S. Pat. Nos. 5,643,192; 5,795,780 and 6,472,162; and Kaetsu et al., *Thrombosis Research*, 90:1001-109 (1998). Additional exemplary precipitation agents include, but are not limited to, non-detergent sulphobetaines (NDSBs) and mild denaturing agents.

An alternative method for concentrating one or more proteins and/or substances from whole blood or blood plasma components such as PPP and/or PRP involves the use of one or more chemical additives to precipitate one or more proteins and/or substances. For example, between about 4% and 20% (vol/vol) ethanol may be used in a chemical precipitation method to isolate at least fibrinogen, albumin, cholesterol and various globulins whole blood, PPP and/or PRP, see, for example, Cohn et al., *J. Am. Chem. Soc.*; 68:459-475 (1946); van Oss, *Journal of Protein Chemistry*, 8:661-668 (1989). Ethanol may added to whole blood or blood plasma components such as PRP or PPP to increase the time it takes a clot to form, e.g., the plasma clotting time. Thus, in one embodiment of the present invention, ethanol may be used to increase the clotting time to about 30 minutes. In addition, ethanol may be used to impact the strength of a biological composition, e.g., a fibrin composition. For example, about 4% to about 20% ethanol may be used to precipitate plasma proteins. Subsequently, the precipitated proteins may be re-dissolved and/or reconstituted in a volume of fresh PRP, PPP, and/or whole blood, for example. It was discovered that the concentration of ethanol used to precipitate such proteins affects the strength of a fibrin composition of the present invention. For example, a fibrin composition prepared using plasma proteins precipitated using about 4% to about 20% ethanol was found to have maximum strength, i.e., maximum mechanical strength.

In one method of the present invention, PPP is chilled to approximately about 4° C. for approximately about 10 minutes. A chemical precipitation agent, e.g., ethanol, is then added to the cooled PPP and the mixture is allowed to incubate, for example, for approximately about 10 minutes. The mixture is then centrifuged for approximately about 5 to 10 minutes at approximately about 4 to 20° C. The supernatant is then decanted. The precipitated and centrifuged pellet of concentrated proteins is resuspended in plasma at a temperature of approximately about 37° C. for approximately about 1 to 10 minutes.

C. Filtration

An alternative method for concentrating one or more proteins and/or substances from whole blood, blood plasma or a component or fraction thereof such as PPP and/or PRP, involves filtration, e.g., centrifugal filtration, hollow fiber filtration, membrane filtration and/or gel filtration. In membrane filtration, the permeate comprises molecules smaller than the pores of the membrane or filter. Methods to encourage permeation of the small molecules through the membrane include, for example, a vacuum, suction or negative pressure on the permeate side, a positive pressure on the concentrating side, gravity and hydrophilic forces. In one embodiment of this method, centrifugation may be employed to encourage permeation. Centrifugation filtration devices for protein concentration useful in the practice of this embodiment include, but are not limited to, iCON™ concentrators (Pierce Biotechnology), Macrosep® centrifugal devices (Pall Corp) and Centricon centrifugal filter units (Millipore). As an alternative, hollow fiber filtration devices can be employed, such as MicroKros® hollow fiber modules (Spectrum Labs). In gel filtration, an absorbing substance, e.g., polyacrylamide beads, concentrates proteins by selectively absorbing or taking up small molecules, e.g, between about 1.8K and 30K MW, and associated water. Alternative filtration techniques may include the use of one or more filter devices, which may remove small molecules and water but retain the desired protein(s), e.g., fibrinogen with a MW of 340 kDa and/or Factor XIII with a MW of 320 kDa. Various filter devices that may be used according to one or more embodiments of the present method include hollow fiber filter devices wherein the sample flows through the lumen of a hollow fiber while small molecules from the sample are passed through the fiber walls, e.g., through pores, thereby concentrating the proteins of interest. Another filtration technique that may be used according to one embodiment of the present method is tangential filtration wherein fluid is forced through a membrane and the small molecules permeate through while large molecules are collected on the membrane surface.

D. Dialysis

An alternative method for concentrating one or more proteins and/or substances from whole blood, blood plasma or a component or fraction thereof such as PPP and/or PRP that may be used includes dialysis, e.g., membrane dialysis. Dialysis may be used, for example, to adjust a protein sample from one buffer to another, in adjusting the metal and salt ion concentrations, and in the removal of unwanted small molecules. In one embodiment, dialysis is used to remove a salt, e.g., ammonium sulfate, previously employed to precipitate a protein or substance of interest. A dialysis membrane is generally made of cellulose acetate. In addition, the membrane is semi-permeable, i.e., molecules below a specified molecular weight can readily pass through the membrane whereas larger molecules cannot. Dialysis membranes are commercially available with a wide variety of molecular weight cutoffs. For example, 10,000 and 40,000 dalton membranes are typically used for protein dialysis.

E. Chromatography

An alternative method for concentrating one or more proteins and/or substances from whole blood, blood plasma or a component or fraction thereof such as PPP and/or PRP is chromatography. Chromatography generally involves a sample, or sample extract, dissolved in a mobile phase, which may be a gas, a liquid or a supercritical fluid, for example. The mobile phase is forced through an immobile, immiscible stationary phase. The phases are chosen such that components of the sample have differing solubilities in each phase. A component that is quite soluble in the stationary phase will take longer to travel through it than a component that is not very soluble in the stationary phase but very soluble in the mobile phase. As a result of these differences in mobilities, sample components will become separated from each other as they travel through the stationary phase. Either the slower mobility or faster mobility components can be chosen for isolation and concentration. One or more forms of chromatography may be used, for example, liquid chromatography, ion exchange chromatography and/or affinity chromatography may be used. Ion exchange chromatography separates charged substances via column materials that carry an opposite charge. The ionic groups of the exchanger column(s) are covalently bound to a gel matrix, for example, and are compensated by small concentrations of counter ions, which are present in a buffer. When a sample is added to the column, an exchange with the weakly bound counter ions takes place. Affinity chromatography separates substances, e.g., biomolecules, via affinity binding. Affinity chromatography can enable purification of a biomolecule, e.g., a protein, with respect to its function and/or individual chemical structure. For example, a substance to be purified or concentrated is specifically and reversibly adsorbed or chemically bound to a ligand or binding substance. The ligand is generally immobilized by a covalent bond to a chromatographic bed material or matrix material. Samples are applied under favorable conditions for their specific binding to the ligand. Substances of interest are consequently bound to the ligand while unbound substances are washed away or removed. Recovery of bound substances of interest may then be achieved by changing experimental conditions to favor desorption from the ligand.

F. Electrophoresis

As an alternative, electrophoresis may be employed to concentrate one or more proteins and/or substances from whole blood, blood plasma or a component or fraction thereof such as PPP and/or PRP. Electrophoresis may be used to separate substances based on size, electric charge and other physical properties. In gel electrophoresis, molecules are forced across a span of gel, motivated by an electrical current. In capillary electrophoresis, the application of high voltages across buffer filled capillaries is used to achieve separations.

G. Dehydration

An alternative method for concentrating one or more proteins and/or substances from whole blood, blood plasma or a component or fraction thereof such as PPP and/or PRP that may be used is dehydration. Dehydration may be used to concentrate plasma proteins by partial or complete removal of water from the blood or plasma. Removing water from blood or plasma increases the concentration of each protein in the blood or plasma. Dehydration may be accomplished, for example, by the addition of energy (heat) to drive out water, by the addition of a material, e.g., hydrophilic polymer materials such as polyacrylamide beads, or by the addition of a dehydration agent, such as an alcohol, which removes and/or absorbs water molecules.

XIII. Fibrin Compositions of the Present Invention

The present invention provides fibrin compositions and methods for making the same. In one embodiment, all of the components of the fibrin composition are autologous, i.e., derived from the patient to whom the fibrin composition is to be administered (the recipient of the composition). In addition, methods are provided for the production of autologous thrombin (AT) and AT compositions for use in the preparation of the fibrin compositions of the invention.

For instance, whole blood can be obtained from a patient using known techniques. Optionally, the whole blood is processed into platelet poor plasma and/or platelet rich plasma. Blood plasma proteins, including thrombin and fibrinogen, are then extracted from the whole blood (and/or components or fractions thereof) and combined to generate an autologous fibrin composition, i.e., a fibrin composition having autologous thrombin and autologous fibrinogen.

In addition, provided herein are fibrin compositions having one or more non-autologous components and/or recombinant components, such as thrombin and/or fibrinogen, as described herein.

In one embodiment, whole blood is collected from the same patient to whom the fibrin composition is to be administered, i.e., the recipient of the composition. Additional sources of whole blood include, for example, single donor human whole blood, pooled human whole blood, human blood products comprising platelets and plasma, e.g., from a blood bank, single donor animal whole blood, pooled animal whole blood and animal blood products comprising platelets and plasma.

In another embodiment, fibrinogen, e.g., autologous fibrinogen, recombinant fibrinogen, is added to a platelet gel composition to accelerate the coagulation of the platelet gel, e.g., to speed up the clotting (gelling) time. Rapid coagulation time is a desired feature of such a fibrin composition, e.g., during controlled delivery of the composition into tissue, as it reduces leakage or backbleed.

FIGS. 2-7 are flow diagrams of various embodiments of fibrin compositions, which are further detailed below, in accordance with the present invention.

A. PPP-Thrombin, PRP, PPP-Protein:

Platelet rich plasma (PRP) and platelet poor plasma (PPP) are formed, for example, by centrifuging a quantity of anti-coagulated whole blood, e.g., that was previously drawn from the patient. The PPP is then divided into two portions. Thrombin is then derived from the first portion of the PPP. One or more proteins, e.g., fibrinogen, is concentrated and removed from the second portion of the PPP. The thrombin, the concentrated protein and the PRP are then mixed together to form a fibrin sealant composition according to one embodiment of the present invention.

Alternatively, PRP and PPP are formed, for example, by centrifuging a quantity of anticoagulated whole blood, e.g., that was previously drawn from the patient. One or more proteins, e.g., fibrinogen, is concentrated and removed from the PPP. Thrombin is then derived from the PPP resulting from the protein concentration process. The thrombin, the concentrated protein and the PRP are then mixed together to form a fibrin sealant composition.

PPP may be divided into two portions. Thrombin, e.g., autologous thrombin, may then be derived from the first portion of the PPP. For example, a compound that reverses the effect of the anticoagulant present in the PPP may be added to the first portion of PPP, and a clot or coagulated mass may be allowed to form. The clot or coagulated mass may then be triturated and the resulting serum, containing thrombin, may be collected. One or more proteins, e.g., fibrinogen, is concentrated, for example, as described herein, and removed from the second portion of the PPP. The thrombin, the concentrated protein and the PRP are then mixed together to form a fibrin composition. If the concentrated protein comprises fibrinogen, then the fibrin composition may be used, for example, as a platelet rich fibrin sealant composition.

In one embodiment of the present invention, one or more proteins, e.g., fibrinogen, is concentrated, for example, as described herein, and removed from the PPP. Thrombin is then derived from the PPP resulting from the protein concentration process. For example, a compound that reverses the effect of the anticoagulant present in the resultant PPP may be added and a clot or coagulated mass may be allowed to form. The clot or coagulated mass may then be triturated and the resulting serum, containing thrombin, may be collected. The thrombin, the concentrated protein and the PRP are then mixed together to form a fibrin composition according to one embodiment of the present invention. If the concentrated protein comprises fibrinogen, then the fibrin composition may be used, for example, as a platelet rich fibrin sealant composition.

B. PRP-Thrombin, PRP, PPP-Protein:

As an alternative, PRP and PPP are formed, for example, by centrifuging a quantity of anticoagulated whole blood, e.g., that was previously drawn from the patient. The PRP is then divided into two portions. Thrombin is then derived from the first portion of the PRP. One or more proteins, e.g., fibrinogen, is concentrated and removed from the PPP. The thrombin, the concentrated protein and the second portion of the PRP are then mixed together to form a fibrin sealant composition.

In one embodiment of the present invention, PRP may be divided into two portions. Thrombin, e.g., autologous thrombin, may then be derived from the first portion of the PRP. For example, a compound that reverses the effect of the anticoagulant present in the PPP may be added to the first portion of PPP, and a clot or coagulated mass may be allowed to form. The clot or coagulated mass may then be triturated and the resulting serum, containing thrombin, may be collected. One or more proteins, e.g., fibrinogen, is concentrated, for example, as described herein, and removed from the PPP. The thrombin, the concentrated protein and the second portion of the PRP are then mixed together to form a fibrin composition according to one embodiment of the present invention. If the concentrated protein comprises fibrinogen, then the fibrin composition may be, for example, used as a platelet rich fibrin sealant composition.

C. R-Thrombin, PRP, PPP-Protein:

In another alternative embodiment of the present invention, PRP and PPP are formed, for example, by centrifuging a quantity of anticoagulated whole blood, e.g., that was previously drawn from the patient. One or more proteins, e.g., fibrinogen, is concentrated, for example, as described herein, and removed from the PPP. Recombinant thrombin, the concentrated protein and the PRP are then mixed together to form a fibrin composition according to one embodiment of the present invention. If the concentrated protein comprises fibrinogen, then the fibrin composition may be used, for example, as a platelet rich fibrin sealant composition.

D. PPP-Thrombin, PRP, PRP-Protein:

In another alternative embodiment of the present invention, PRP and PPP are formed, for example, by centrifuging a quantity of anticoagulated whole blood, e.g., that was previously drawn from the patient. Thrombin is then derived from the PPP. For example, a compound that reverses the effect of the anticoagulant present in the PPP may be added to the PPP, and a clot or coagulated mass may be allowed to form. The clot or coagulated mass may then be triturated and the resulting serum, containing thrombin, may be collected. The PRP is then divided into two portions. One or more proteins, e.g., fibrinogen, is concentrated, for example, as described herein, and removed from the first portion of PRP. The thrombin, the concentrated protein and the second portion of PRP are then mixed together to form a fibrin composition according to one embodiment of the present invention. If the concentrated protein comprises fibrinogen, then the fibrin composition may be used, for example, as a platelet rich fibrin sealant composition.

E. PRP-Thrombin, PRP, PRP-Protein:

In another alternative embodiment of the present invention, PRP is formed, for example, by centrifuging a quantity of anticoagulated whole blood, e.g., that was previously drawn from the patient. The PRP is then divided into three portions. Thrombin is then derived from the first portion of the PRP. For example, a compound that reverses the effect of the anticoagulant present in the PRP may be added to the first portion of PRP, and a clot or coagulated mass may be allowed to form. The clot or coagulated mass may then be triturated and the resulting serum, containing thrombin, may be collected. One or more proteins, e.g., fibrinogen, is concentrated, for example, as described herein, and removed from the second portion of PRP. The thrombin, the concentrated protein and the third portion of PRP are then mixed together to form a fibrin composition according to one embodiment of the present invention. If the concentrated protein comprises fibrinogen, then the fibrin composition may be used, for example, as a platelet rich fibrin sealant composition.

In another alternative embodiment of the present invention, PRP is formed, for example, by centrifuging a quantity of anticoagulated whole blood, e.g., that was previously drawn from the patient. The PRP is then divided into two portions. One or more proteins, e.g., fibrinogen, is concentrated, for example, as described herein, and removed from the first portion of PRP. Thrombin is then derived from the PRP resulting from the protein concentration process. For example, a compound that reverses the effect of the anticoagulant present in the resultant PRP may be added to the PRP, and a clot or coagulated mass may be allowed to form. The clot or coagulated mass may then be triturated and the resulting serum, containing thrombin, may be collected. The thrombin, the concentrated protein and the second portion of PRP are then mixed together to form a fibrin composition according to one embodiment of the present invention. If the concentrated protein comprises fibrinogen, then the fibrin composition may be used, for example, as a platelet rich fibrin sealant composition.

F. R-Thrombin, PRP, PRP-Protein:

In another alternative embodiment of the present invention, PRP is formed, for example, by centrifuging a quantity of anticoagulated whole blood, e.g., that was previously drawn from the patient. The PRP is then divided into two portions. One or more proteins, e.g., fibrinogen, is concentrated, for example, as described herein, and removed from the first portion of PRP. Recombinant thrombin, the concentrated protein and the second portion of PRP are then mixed together to form a fibrin composition according to one embodiment of the present invention. If the concentrated protein comprises fibrinogen, then the fibrin composition may be used, for example, as a platelet rich fibrin sealant composition.

G. PPP-Thrombin, PRP, R-Protein:

In another alternative embodiment of the present invention, PRP and PPP are formed, for example, by centrifuging a quantity of anticoagulated whole blood, e.g., that was previously drawn from the patient. Thrombin is then derived from the PPP. For example, a compound that reverses the effect of the anticoagulant present in the PPP may be added to the PPP, and a clot or coagulated mass may be allowed to form. The clot or coagulated mass may then be triturated and the resulting serum, containing thrombin, may be collected. The thrombin, one or more recombinant proteins, e.g., recombinant fibrinogen, and PRP are then mixed together to form a fibrin composition according to one embodiment of the present invention. If the concentrated protein comprises fibrinogen, then the fibrin composition may be used, for example, as a platelet rich fibrin sealant composition.

H. PRP-Thrombin, PRP, R-Protein:

In another alternative embodiment of the present invention, PRP is formed, for example, by centrifuging a quantity of anticoagulated whole blood, e.g., that was previously drawn from the patient. The PRP is then divided into two portions. Thrombin is then derived from the first portion of the PRP. For example, a compound that reverses the effect of the anticoagulant present in the PRP may be added to the PRP, and a clot or coagulated mass may be allowed to form. The clot or coagulated mass may then be triturated and the resulting serum, containing thrombin, may be collected. The thrombin, one or more recombinant proteins, e.g., recombinant fibrinogen, and the second portion of the PRP are then mixed together to form a fibrin composition according to one embodiment of the present invention. If the concentrated protein comprises fibrinogen, then the fibrin composition may be used, for example, as a platelet rich fibrin sealant composition.

I. R-Thrombin, PRP, R-Protein:

In another alternative embodiment of the present invention, PRP is formed, for example, by centrifuging a quantity of anticoagulated whole blood, e.g., that was previously drawn from the patient. Recombinant thrombin, one or more recombinant proteins, e.g., recombinant fibrinogen, and PRP are mixed together to form a fibrin composition according to one embodiment of the present invention. If the concentrated protein comprises fibrinogen, then the fibrin composition may be used, for example, as a platelet rich fibrin sealant composition.

J. PPP-Thrombin, PPP, PPP-Protein:

In another alternative embodiment of the present invention, PPP is formed, for example, by centrifuging a quantity of anticoagulated whole blood, e.g., that was previously drawn from the patient. The PPP is then divided into three portions. Thrombin is then derived from the first portion of the PPP. For example, a compound that reverses the effect of the anticoagulant present in the PPP may be added to the PPP, and a clot or coagulated mass may be allowed to form. The clot or coagulated mass may then be triturated and the resulting serum, containing thrombin, may be collected. One or more proteins, e.g., fibrinogen, is concentrated, for example, as described herein, and removed from the second portion of the PPP. The thrombin, the concentrated protein and the third portion of PPP are then mixed together to form a fibrin composition according to one embodiment of the present invention. If the concentrated protein comprises fibrinogen, then the fibrin composition may be used, for example, as a platelet poor fibrin sealant composition.

In another alternative embodiment of the present invention, PPP is formed, for example, by centrifuging a quantity of anticoagulated whole blood, e.g., that was previously drawn from the patient. The PPP is then divided into two portions. One or more proteins, e.g., fibrinogen, is concentrated, for example, as described herein, and removed from the first portion of the PPP. Thrombin is then derived from the PPP resulting from the protein concentration process. For example, a compound that reverses the effect of the anticoagulant present in the resultant PPP may be added to the PPP, and a clot or coagulated mass may be allowed to form. The clot or coagulated mass may then be triturated and the resulting serum, containing thrombin, may be collected. The thrombin, the concentrated protein and the second portion of PPP are then mixed together to form a fibrin composition according to one embodiment of the present invention. If the concentrated protein comprises fibrinogen, then the fibrin composition may be used, for example, as a platelet poor fibrin sealant composition.

K. PRP-Thrombin, PPP, PPP-Protein:

In another alternative embodiment of the present invention, PRP and PPP are formed, for example, by centrifuging a quantity of anticoagulated whole blood, e.g., that was previously drawn from the patient. Thrombin is then derived from the PRP. For example, a compound that reverses the effect of the anticoagulant present in the PRP may be added to the PRP, and a clot or coagulated mass may be allowed to form. The clot or coagulated mass may then be triturated and the resulting serum, containing thrombin, may be collected. The PPP is divided into two portions. One or more proteins, e.g., fibrinogen, is concentrated, for example, as described herein, and removed from the first portion of the PPP. The thrombin, the concentrated protein and the second portion of the PPP are then mixed together to form a fibrin composition according to one embodiment of the present invention. If the concentrated protein comprises fibrinogen, then the fibrin composition may be used, for example, as a platelet poor fibrin sealant composition.

L. R-Thrombin, PPP, PPP-Protein:

In another alternative embodiment of the present invention, PPP is formed, for example, by centrifuging a quantity of anticoagulated whole blood, e.g., that was previously drawn from the patient. The PPP is then divided into two portions. One or more proteins, e.g., fibrinogen, is concentrated, for example, as described herein, and removed from the first portion of the PPP. Recombinant thrombin, the concentrated protein and the second portion of the PPP are then mixed together to form a fibrin composition according to one embodiment of the present invention. If the concentrated protein comprises fibrinogen, then the fibrin composition may be used, for example, as a platelet poor fibrin sealant composition.

M. PPP-Thrombin, PPP, PRP-Protein:

In another alternative embodiment of the present invention, PRP and PPP are formed, for example, by centrifuiging a quantity of anticoagulated whole blood, e.g., that was previously drawn from the patient. The PPP is then divided into two portions. Thrombin is then derived from the first portion of the PPP. For example, a compound that reverses the effect of the anticoagulant present in the PPP may be added to the PPP, and a clot or coagulated mass may be allowed to form. The clot or coagulated mass may then be triturated and the resulting serum, containing thrombin, may be collected. One or more proteins, e.g., fibrinogen, is concentrated, for example, as described herein, and removed from the PRP. The thrombin, the concentrated protein and the second portion of PPP are then mixed together to form a fibrin composition according to one embodiment of the present invention. If the concentrated protein comprises fibrinogen, then the fibrin composition may be used, for example, as a platelet poor fibrin sealant composition.

N. PRP-Thrombin, PPP, PRP-Protein:

In another alternative embodiment of the present invention, PRP and PPP are formed, for example, by centrifuging a quantity of anticoagulated whole blood, e.g., that was previously drawn from the patient. The PRP is then divided into two portions. Thrombin is then derived from the first portion of the PRP. For example, a compound that reverses the effect of the anticoagulant present in the PRP may be added to the PRP, and a clot or coagulated mass may be allowed to form. The clot or coagulated mass may then be triturated and the resulting serum, containing thrombin, may be collected. One or more proteins, e.g., fibrinogen, is concentrated, for example, as described herein, and removed from the second portion of the PRP. The thrombin, the concentrated protein and the PPP are then mixed together to form a fibrin composition according to one embodiment of the present invention. If the concentrated protein comprises fibrinogen, then the fibrin composition may be used, for example, as a platelet poor fibrin sealant composition.

In another alternative embodiment of the present invention, PRP and PPP are formed, for example, by centrifuging a quantity of anticoagulated whole blood, e.g., that was previously drawn from the patient. One or more proteins, e.g., fibrinogen, is concentrated, for example, as described herein, and removed from the PRP. Thrombin is then derived from the PRP resulting from the protein concentration process. For example, a compound that reverses the effect of the anticoagulant present in the resultant PRP may be added to the PRP, and a clot or coagulated mass may be allowed to form. The clot or coagulated mass may then be triturated and the resulting serum, containing thrombin, may be collected. The thrombin, the concentrated protein and the PPP are then mixed together to form a fibrin composition according to one embodiment of the present invention. If the concentrated protein comprises fibrinogen, then the fibrin composition may be used, for example, as a platelet poor fibrin sealant composition.

O. R-Thrombin, PPP, PRP-Protein:

In another alternative embodiment of the present invention, PRP and PPP are formed, for example, by centrifuging a quantity of anticoagulated whole blood, e.g., that was previously drawn from the patient. One or more proteins, e.g., fibrinogen, is concentrated, for example, as described herein, and removed from the PRP. Recombinant thrombin, the concentrated protein and the PPP are then mixed together to form a fibrin composition according to one embodiment of the present invention. If the concentrated protein comprises fibrinogen, then the fibrin composition may be used, for example, as a platelet poor fibrin sealant composition.

P. PPP-Thrombin, PPP, R-Protein:

In another alternative embodiment of the present invention, PPP is formed, for example, by centrifuging a quantity of anticoagulated whole blood, e.g., that was previously drawn from the patient. The PPP is then divided into two portions. Thrombin is then derived from the first portion of the PPP. For example, a compound that reverses the effect of the anticoagulant present in the PPP may be added to the PPP, and a clot or coagulated mass may be allowed to form. The clot or coagulated mass may then be triturated and the resulting serum, containing thrombin, may be collected. The thrombin, one or more recombinant proteins, e.g., recombinant fibrinogen, and the second portion of the PPP are then mixed together to form a fibrin composition according to one embodiment of the present invention. If the concentrated protein comprises fibrinogen, then the fibrin composition may be used, for example, as a platelet poor fibrin sealant composition.

Q. PRP-Thrombin, PPP, R-Protein:

In another alternative embodiment of the present invention, PRP and PPP are formed, for example, by centrifuging a quantity of anticoagulated whole blood, e.g., that was previously drawn from the patient. Thrombin is then derived from the PRP. For example, a compound that reverses the effect of the anticoagulant present in the PRP may be added to the PRP, and a clot or coagulated mass may be allowed to form. The clot or coagulated mass may then be triturated and the resulting serum, containing thrombin, may be collected. The thrombin, one or more recombinant proteins, e.g., recombinant fibrinogen, and PPP are then mixed together to form a fibrin composition according to one embodiment of the present invention. If the concentrated protein comprises fibrinogen, then the fibrin composition may be used, for example, as a platelet poor fibrin sealant composition.

R. R-Thrombin, PPP, R-Protein:

In another alternative embodiment of the present invention, PPP is formed, for example, by centrifuging a quantity of anticoagulated whole blood, e.g., that was previously drawn from the patient. Recombinant thrombin, one or more recombinant proteins, e.g., recombinant fibrinogen, and PPP are mixed together to form a fibrin composition according to one embodiment of the present invention. If the concentrated protein comprises fibrinogen, then the fibrin composition may be used, for example, as a platelet poor fibrin sealant composition.

XIV. Therapeutic Applications for the Compositions of the Invention

A composition of the present invention may be used as a haemostatic agent, for sealing a wound such as a surgical wound or a chronic wound, e.g., a chronic ulcer, a wound healing agent, e.g., a cutaneous wound healing agent, and/or agents or vehicles for the delivery of one or more cells, pharmaceutical agents, therapeutic agents, medical agents and/or biological agents. For example, a composition of the present invention may be used in plastic surgery or bone repair and/or reconstruction. In another embodiment, a composition, e.g., a fibrin composition, may be injected into heart tissue, e.g., myocardial tissue. The injection of a fibrin composition of the present invention into tissue may provide many features and promoters of healthy healing of injured or diseased tissue.

A composition of the present invention may provide many biologically active agents that can facilitate healthy healing of tissue and potentially local regeneration of tissue. A number of agents may be found in one embodiment of the present invention, platelet agents such as, for example, cytokines (including IL-13, IL-6, TNF-α), chemokines (including ENA-78 (CXCL5), IL-8 (CXCL8), MCP-3 (CCL7), MIP-1α (CCL3), NAP-2 (CXCL7), PF4 (CXCL4), RANTES (CCL5)), inflammatory mediators (including PGE2), matrix metalloproteinases, and growth factors (including Angiopoitin-1, bFGF, EGF, HGF, IGF-I, IGF-II, PDGF AA and BB, TGF-β1, 2, and 3, and VEGF). Multiple agents found in a fibrin composition of the present invention may have an effect in regards to facilitating wound healing. For example, one or more agents found in a fibrin composition of the present invention may play a role in the recruitment of circulating cells to the injured site. One or more agents found in a fibrin composition of the present invention may play a role in the stimulation of local angiogenesis. It is believed that the various agents that may be found in a fibrin composition of the present invention may promote healthy remodeling of injured tissue.

In one embodiment of the present invention, a composition of the present invention may be used to improve cell retention and cell survival in a cell transplantation technique. For example, a fibrin composition of the invention may provide a very rich growth medium for the transplanted cells and/or help hold the transplanted cells in place until they have had a chance to integrate into the target tissue. A fibrin composition of the present invention may prevent injected or transplanted cells from being "washed out" soon after injection or delivery.

XV. Dosages and Routes of Administration

In certain embodiments, the compositions disclosed herein include pharmaceutical agents, therapeutic agents, medical agents and/or biological agents that may be administered at dosages of at least about 0.01 to about 100 mg/kg, about 0.1 to about 50 mg/kg, or about 0.1 to about 30 mg/kg, of body weight, although other dosages may be administered. The amount administered may vary depending on various factors including, but not limited to, a particular agent chosen, the disease, and whether prevention or treatment is to be achieved.

In certain embodiments, compositions disclosed herein include sense or antisense nucleic acid molecules. Administration of sense or antisense nucleic acid molecules may be accomplished through the administration of the nucleic acid molecule (see, for example, Felgner et al., U.S. Pat. No. 5,580,859; Pardoll et al., *Immunity*, 33:165 (1995); Stevenson et al., *Immunol., Rev.*, 145: 211 (1995); Molling, *Mol. Med.*, 75: 242 (1997); Donnelly et al., *Ann. N.Y. Acad. Sci.*, 772: 40 (1995); Yang et al., *Mol. Med. Today*, 2: 476 (1996); Abdallah et al., *Biol Cell*, 85: 1 (1995); Wolff et al., *Science* 247: 1465 (1990); Tripathy et al., *PNAS*, 91: 11557 (1994); Tripathy et al., *PNAS*, 93: 10876 (1996); Tripathy et al., *Nature Med.*, 2, 545 (1996); Tsurumi et al., *Cir.*, 94: 3281 (1996); Baumgartner et al., *Circulation*, 96: 1 (1997); Lin et al., *Hypertension*, 26: 847 (1990)). Pharmaceutical formulations, dosages and routes of administration for nucleic acids are generally disclosed, for example, in Feigner et al., supra.

The amount of cells, pharmaceutical agents, therapeutic agents, medical agents and/or biological agents administered via a composition of the present invention is selected based on the particular indication to be treated. The compositions of the invention may also amenable to chronic use for prophylactic purposes.

A composition of the present invention may be injected epicardially, endocardially, transvascularly and/or percutaneously. In one embodiment, a physician may perform one or more epicardial injections of a fibrin composition into tissue (e.g, via open chest surgery, thoracoscopic surgery, or subxiphoid access surgery), or a physician may perform one or more endocardial or transvascular injections of a fibrin composition into tissue (e.g., via a percutaneous approach). In another embodiment, a physician may perform one or more intramyocardial injections of a fibrin composition, by epicardially, endocardially, transvascularly (percutaneous) routes. In yet another embodiment, a fibrin composition may be injected or delivered into injured, wounded and/or ischemic tissue, e.g., ischemic cardiac tissue. In another embodiment, a fibrin composition may be injected into aneurysms and/or pseudo aneurysms to relieve pressure and facilitate vessel healing. In addition, a fibrin composition may be injected into an aneurysmic sac during stenting (e.g., AAA stenting) to relieve pressure, facilitate healing of a vessel and prevention of leaks, e.g., endoleaks.

The invention has been described with reference to various embodiments and will be further described by reference to the following detailed examples. It is understood, however, that there are many extensions, variations, and modifications on the basic theme of the present invention beyond that shown in the examples and detailed description, which are within the spirit and scope of the present invention.

EXAMPLES

The present invention will now be described with reference to the following specific, non-limiting examples:

Example 1

Autologous Thrombin Composition and Method of Preparation

An autologous thrombin composition having an extended table-life is prepared from a single donor's whole blood, blood components, or a combination thereof. Non-anticoagulated whole blood, anticoagulated whole blood, or components thereof such as platelet-rich plasma, platelet-poor plasma, and/or platelet-free plasma obtained from the donor is aspirated into a chamber or vessel. If anticoagulated whole blood or a component thereof is used, it is contacted with an effective amount of a compound or material that reverses the anticoagulant. Clotting is initiated and/or accelerated by the use of a contact activation agent, e.g., an agent that initiates clotting via the intrinsic clotting cascade or pathway, such as glass, diatomaceous earth, ceramic, kaolin, and the like. Complete clotting is achieved within twenty minutes at room temperature, which time may be accelerated by increasing the temperature, for example, to physiological temperature levels, e.g., 37° C. As an alternative or in addition thereto, one or more extrinsic coagulation pathway initiation agents, i.e., an agent that initiates clotting via the extrinsic clotting cascade or pathway, such as thromboplastin, a phospholipid, a derivative thereof, or a combination thereof, is used to initiate and/or accelerate clotting.

For example, whole blood from a single donor is contacted with thromboplastin, glass and calcium chloride. A clot is generated within about 5 minutes or less, e.g., within about 2 to about 4 minutes, at room temperature. Thrombin is then harvested from the clot by squeezing the clot, filtering the thrombin-rich serum, and contacting the thrombin with a stabilization agent, e.g., an alcohol such as ethanol, to preserve its biological activity, thus providing an autologous thrombin composition having an extended table-life. Contacting thrombin with ethanol, e.g., 15% to 25% v/v ethanol, has been shown by the inventors to preserve the biological activity of the thrombin by at least 3 hours. Biological activity of the thrombin may be preserved further, for more than three hours, by refrigerating the thrombin-ethanol mixture for example, storing the mixture at 4° C.

Contacting the autologous thrombin composition with platelet rich plasma, platelet poor plasma, and/or whole blood dilutes the concentration of ethanol present in the composition to a level that does not inhibit the formation of a gel, and an autologous platelet gel is provided.

In experiments using the autologous thrombin composition prepared by method, an autologous platelet gel was formed in less than 20 seconds, even using an autologous thrombin composition that had been stored for three hours. In addition, after six hours of refrigeration, the autologous thrombin composition triggered autologous platelet gel formation after contact with each of PRP and PPP. Thrombin-rich serum, after storage at room temperature, may trigger gel formation with PRP and/or PPP after 24 hours.

Thrombin-rich serum may be used to form a gel with whole blood, PRP, PPP, pooled plasma, fresh frozen plasma, and/or cryo precipitate. In addition, thrombin-rich serum may be combined with other activators, or scaffolding substances like collagen and delivered as a hemostatic agent and/or as a wound healing agent, for example. The thrombin-rich serum may be used to treat aneurysms, or pseudo-aneurysms, or as an adjunct to stent grafting by clotting off the aneurismal sac thereby preventing the occurrence of endoleaks or sac ruptures. In addition, the thrombin-rich serum may be used as a topical hemostat to prevent oozing from organs.

Example 2

Customizable Fibrin Compositions

PRP and PPP, e.g., autologous PRP and PPP, are prepared from anticoagulated whole blood, for example, as described herein. A concentrated plasma (plasma concentrate) rich in clotting proteins, such as, but not limited to, fibrinogen, Factor XIII, Factor VIII, and vWF, is prepared from the PPP fraction.

In one embodiment of the present invention, an organic reagent, such as ethanol, isopropanol or PEG, may be used to precipitate one or more substances, e.g., clotting proteins, followed by centrifugation and/or filtration. One or more substance, e.g., clotting proteins, may also be concentrated by precipitation using an inorganic salt(s) or a salt solution(s), such as ammonium sulfate. In one embodiment of the present invention, a filter device may be employed to remove water and small molecules from the plasma upon application of a pressure differential. The plasma concentrate, PRP and thrombin may then be combined in various ratios to prepare customizable fibrin compositions that may be useful for promoting wound healing, hemostasis and sealing. The plasma concentrate is combined with thrombin to prepare a fibrin composition. PRP is combined with thrombin to prepare an autologous platelet gel (APG).

In one embodiment of the present invention, the plasma concentrate may be subjected to one or more additional steps (pre and/or post treatment steps) to further concentrate one or more substance, e.g., clotting proteins. In one embodiment of the present invention, the PRP fraction may be subjected to additional one or more additional steps (pre-treatment steps), prior to contacting PRP with the plasma concentrate, to release growth factors into the plasma concentrate matrix.

All publications, patents and patent applications are incorporated herein by reference. While in the foregoing specification this invention has been described in relation to certain embodiments thereof, and many details have been set forth for purposes of illustration, it will be apparent to those skilled in the art that the invention is susceptible to additional embodiments and that certain of the details described herein may be varied considerably without departing from the basic principles of the invention.

What is claimed is:

1. A method of preparing a fibrin composition, the method consisting of:
    contacting a first portion of an anticoagulated whole blood, a fraction of the anticoagulated whole blood, or a component of the anticoagulated whole blood with a contact activation agent and an extrinsic coagulation pathway initiation agent to provide a coagulated mass in less than about 30 minutes;
    extracting thrombin from the coagulated mass to provide a thrombin composition;
    fractionating a second portion of the anticoagulated whole blood, the fraction of the anticoagulated whole blood, or the component of the anticoagulated whole blood to obtain a fibrinogen composition and a platelet plasma composition;
    contacting the fibrinogen composition, platelet plasma composition, or a combination thereof with a recombinant protein composition;
    contacting the thrombin composition with a stabilizing agent to provide a thrombin composition having a table-life of more than about 6 hours, wherein the anticoagulated whole blood, a fraction thereof or a component thereof is not contacted with the stabilizing agent during the generation of the coagulated mass;
    contacting the thrombin composition, the fibrinogen composition and the platelet plasma composition to generate a fibrin composition; and
    adding at least one micro-particle to the fibrin composition, wherein the at least one micro-particle includes at least one of the following: a pharmaceutical agent, a therapeutic agent, a medical agent, a biological agent, and any combination thereof;
    adding at least one protecting group to protect one or more functional groups of at least one of the following: the thrombin composition, the fibrinogen composition, the platelet plasma composition, and the fibrin composition, wherein the protecting group includes at least one of the following: a carbonyl protecting group, an alcohol protecting group, and an amine protecting group.

2. The method of claim 1, wherein the stabilizing agent comprises a polyol, PEG, ammonium sulfate, a non-polar solvent, a polar solvent, a methyl isobutyl ketone alcohol, glycol, tricloroacetic acid, acetate salt, or any combination thereof.

3. The method of claim 2, wherein the stabilizing agent comprises ethanol.

4. The method of claim 3, wherein about 8% to about 25% volume/volume ethanol is added to the thrombin composition.

5. The method of claim 4, wherein about 10% volume/volume ethanol is added to the thrombin composition.

6. The method of claim 1, wherein the thrombin composition has a table-life of more than 12 hours.

7. The method of claim 6, wherein the thrombin composition has a table-life of from more than 12 up to 24 hours.

8. The method of claim 1, wherein the coagulated mass is generated in less than about 10 minutes.

9. The method of claim 8, wherein the coagulated mass is generated in less than about 5 minutes.

10. The method of claim 9, wherein the coagulated mass is generated in less than about 3 minutes.

11. The method of claim 10, wherein the coagulated mass is generated in about 1 minute to about 3 minutes.

12. The method of claim 1, wherein the first portion is a portion of the anticoagulated whole blood, a portion of the fraction of the anticoagulated whole blood or a portion of the component of the anticoagulated whole blood and comprises platelet rich plasma (PRP), platelet poor plasma (PPP), or a combination thereof.

13. The method of claim 12, wherein the first portion is a portion of the anticoagulated whole blood, a portion of the fraction of the anticoagulated whole blood or a portion of the component of the anticoagulated whole blood and comprises platelet rich plasma (PRP).

14. The method of claim 12, wherein the first portion is a portion of the anticoagulated whole blood, a portion of the fraction of the anticoagulated whole blood or a portion of the component of the anticoagulated whole blood and comprises platelet poor plasma (PPP).

15. The method of claim 1, wherein the second portion is a portion of the anticoagulated whole blood, a portion of the fraction of the anticoagulated whole blood or a portion of the component of the anticoagulated whole blood and comprises platelet rich plasma (PRP), platelet poor plasma (PPP), or a combination thereof.

16. The method of claim 15, wherein the second portion is a portion of the anticoagulated whole blood, a portion of the fraction of the anticoagulated whole blood or a portion of the component of the anticoagulated whole blood and comprises platelet rich plasma (PRP).

* * * * *